(12) United States Patent
Grandis et al.

(10) Patent No.: US 9,926,605 B2
(45) Date of Patent: Mar. 27, 2018

(54) FUNCTIONAL GENOMICS SCREENING PLATFORM FOR HEAD AND NECK CANCER

(71) Applicant: University of Pittsburgh—of the Commonwealth System of Higher Education, Pittsburgh, PA (US)

(72) Inventors: Jennifer R. Grandis, Pittsburgh, PA (US); Vivian Wai Yan Lui, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/604,310

(22) Filed: Jan. 23, 2015

(65) Prior Publication Data
US 2015/0240317 A1  Aug. 27, 2015

Related U.S. Application Data

(63) Continuation of application No. PCT/US2013/051866, filed on Jul. 24, 2013.

(60) Provisional application No. 61/675,667, filed on Jul. 25, 2012.

(51) Int. Cl.
| | |
|---|---|
| *C12Q 1/68* | (2006.01) |
| *A61K 31/506* | (2006.01) |
| *C12N 5/09* | (2010.01) |
| *C12N 15/63* | (2006.01) |

(52) U.S. Cl.
CPC .......... *C12Q 1/6886* (2013.01); *A61K 31/506* (2013.01); *C12Q 2600/106* (2013.01); *C12Q 2600/136* (2013.01); *C12Q 2600/156* (2013.01)

(58) Field of Classification Search
None
See application file for complete search history.

(56) References Cited

FOREIGN PATENT DOCUMENTS

WO   WO 2011/109625 A1   9/2011

OTHER PUBLICATIONS

Meissner et al., "Defects in the Human Leukocyte Antigen Class I Antigen-Processing Machinery in Head and Neck Squamous Cell Carcinoma: Association with Clinical Outcome" 11(7) Clinical Cancer Research (2005).*

Park et al., "Molecular changes in the multistage pathogenesis of head and neck cancer" 9 Cancer Biomarkers 325-339 (2011).*
Gubanova et al., "Downregulation of SMG-1 in HPV-Positive Head and Neck Squamous Cell Carcinoma Due to Promoter Hypermethylation Correlates with Improved Survival" 18(5) Clinical Cancer Research (1257-1267 (Jan. 13, 2012).*
Agrawal et al., "Exome Sequencing of Head and Neck Squamous Cell Carcinoma Reveals Inactivating Mutations in NOTCH1," Science 2011;333(6046):1154-7.
Ashkenazy et al., "ConSurf 2010: calculating evolutionary conservation in sequence and structure of proteins and nucleic acids," Nucl. Acids Res. 38, W529-W533 (2010).
Barr et al., "Large-Scale Structural Analysis of the Classical Human Protein Tyrosine Phosphatome," Cell 2009;136:352-63.
Barretina et al., "The Cancer Cell Line Encyclopedia enables predictive modelling of anticancer drug sensitivity," Nature 2012;483(7391):603-7.
Cerami et al., "The cBio Cancer Genomics Portal: An Open Platform for Exploring Multidimensional Cancer Genomics Data," Cancer Discovery 2012;2:401-4.
Chan et al., "The protein tyrosine phosphatase receptor D, a broadly inactivated tumor suppressor regulating STAT function," Cell Cycle. 2009;8(19):3063-4.
Chaturvedi et al., "Human Papillomavirus and Rising Oropharyngeal Cancer Incidence in the United States," J Clin Oncol. 2011;29(32):4294-301.
Cheung et al., "High frequency of PIK3R1 and PIK3R2 Mutations in Endometrial Cancer Elucidates a Novel Mechanism for Regulation of PTEN Protein Stability," Cancer Discovery. 2011;1(2):170-85.
Giefing et al., "High resolution ArrayCGH and Expression Profiling Identifies PTPRD and PCDH17/PCH68 as Tumor Suppressor Gene Candidates in Laryngeal Squamous Cell Carcinoma," Genes, Chromosomes & Cancer 2011;50(3):154-66.
Grandis et al., "Requirement of Stat3 but not Stat1 Activation for Epidermal Growth Factor Receptor—Mediated Cell Growth In Vitro," J Clin Invest. 1998;102(7):1385-92.
Grandis, "Targeting Oncogenic Pathways in Head & Neck Cancer", Powerpoint Presentation on Apr. 24, 2012.
Groesser et al., "Postzygotic HRAS and KRAS mutations cause nevus sebaceous and Schimmelpenning syndrome," Nat Genet. 2012;44(7):783-7.
Hedvat et al., "The JAK2 Inhibitor AZD1480 Potently Blocks Stat3 Signaling and Oncogenesis in Solid Tumors," Cancer Cell 2009;16(6):487-97.
Hou et al., "Estrogen-sensitive PTPRO Expression Represses Hepatocellular Carcinoma Progression by Control of STAT3," Hepatology 2013;57(2):678-688.
International Search Report dated Oct. 8, 2013 in International Application No. PCT/US2013/051866.

(Continued)

*Primary Examiner* — Nancy J Leith
(74) *Attorney, Agent, or Firm* — Baker Botts L.L.P.

(57) ABSTRACT

The present invention relates to HPV-positive as well as HPV-negative screening platforms that are highly serum-dependent, for use as HNSCC models. These HNSCC models die reproducibly in serum-deprived conditions and the introduction of driver mutations (or increased levels of the WT gene) confers enhanced cell survival and proliferation under serum deprivation. These platforms have the major advantages of allowing functional screening of mutations in relevant HNSCC models (HPV-positive and HPV-negative). In addition to oncogene screening, this model can also be used in drug discovery. Specifically, cells expressing mutations that confer increased survival can then be screened against panels of therapeutic agents to determine if the mutation(s) can predict the optimal treatment for patients whose tumors harbor the mutation(s).

7 Claims, 25 Drawing Sheets

(56) References Cited

OTHER PUBLICATIONS

Figure 1A:
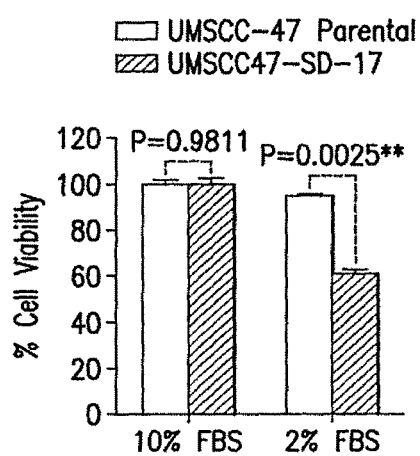

Ioannidis et al., "Discovery of 5-chloro-N2-[(1S)-1-(5-fluoropyrimidin-2-yl)ethyl]-N4-(5-methyl-1H-pyrazol-3-y1)-pyrimidine-2,4-diamine (AZD1480) as a Novel Inhibitor of the Jak/Stat Pathway," J Med Chem. 2011;54(1):262-76.
Kijima et al., "STAT3 Activation Abrogates Growth Factor Dependence and Contributes to Head and Neck Squamous Cell Carcinoma Tumor Growth in Vivo," Cell Growth & Differ. 2002;13(8):355-62.
Kim et al., "Generation of orthotopic and heterotopic human pancreatic cancer xenografts in immunodeficient mice," Nat Protocols 2009;4(11):1670-80.
Lee et al., "Epigenetic modification of SOCS-1 differentially regulates STAT3 activation in response to interleukin-6 receptor and epidermal growth factor receptor signaling through JAK and/or MEK in head and neck squamous cell carcinomas," Mol Cancer Ther. 2006;5(1):8-19.
Leong et al., "Targeted inhibition of Stat3 with a decoy oligonucleotide abrogates head and neck cancer cell growth," Proc Natl Acad Sci USA 2003;100(7):4138-43.
Lim et al., "Synapse formation regulated by protein tyrosine phosphatase receptor T through interaction with cell adhesion molecules and Fyn," EMBO J 2009;28:3564-78.
Lui et al., "Antiproliferative Mechanisms of a Transcription Factor Decoy Targeting Signal Transducer and Activator of Transcription (STAT) 3: The Role of STAT1," Mol. Pharmacol 2007;71:1435-43.
Lui et al., "Frequent Mutation of the PI3K Pathway in Head and Neck Cancer Defines Predictive Biomarkers," Cancer Discovery, Published Online First Apr. 25, 2013, pp. 0F1-0F9 Downloaded from cancerdiscovery.aacrjournals.org on Jul. 2, 2013.
Malinge et al., "Activating mutations in human acute megakaryoblastic leukemia," Blood. 2008;112(10):4220-6.
Moskowitz et al., "Serum biomarker modulation following molecular targeting of epidermal growth factor and cyclooxygenase pathways: A pilot randomized trial in head and neck cancer," Oral Oncol 2012;48:1136-1145.
Murugan et al., "Oncogenic mutations of the PIK3CA gene in head and neck squamous cell carcinomas," International Journal of Oncology 2008;32:101-111.
Paez et al., "EGFR Mutations in Lung Cancer: Correlation with Clinical Response to Gefitinib Therapy," Science 2004;304:1497-500.
Ramqvist et al., "Oropharyngeal Cancer Epidemic and Human Papillomavirus," Emerg Infect Dis. 2010;16(11):1671-7.
Sali et al., "Comparative Protein Modelling by Satisfaction of Spatial Restraints," J Mol. Biol. 1993;234:779-815.
Samuels et al., "Mutant PIK3CA promotes cell growth and invasion of human cancer cells," Cancer Cell, 2005;7:561-573.
Sen et al., "First-in-Human Trial of a STAT3 Decoy Oligonucleotide in Head and Neck Tumors: Implications for Cancer Therapy," Cancer Discovery 2012;2(8):694-705.
Sen et al., "Lack of toxicity of a STAT3 decoy oligonucleotide," Cancer Chemother Pharmacol. 2009;63(6):983-95.
Sen et al., "Targeting STAT3 Abrogates EGFR Inhibitor Resistance in Cancer," Clin Can Res. 2012;18(18):4986-4996.
Solomon et al., "Mutational Inactivation of PTPRD in Glioblastoma Multiforme and Malignant Melanoma," Cancer Res. 2008;68(24):10300-6.
Stransky et al., "The Mutational Landscape of Head and Neck Squamous Cell Carcinoma," Science 2011;333:1157-60.
Stronach et al., "HDAC4-Regulated STAT1 Activation Mediates Platinum Resistance in Ovarian Cancer," Cancer Research 2011;71(13):4412-22.
Veeriah et al., "The tyrosine phosphatase PTPRD is a tumor suppressor that is frequently inactivated and mutated in glioblastoma and other human cancers," Proc Natl Acad Sci USA 2009; 106(23): 9435-40.
Wald et al., "Human papillomavirus alters microRNA profiles in squamous cell carcinoma of the head and neck (SCCHN) cell lines," Head and Neck 2011;33(4):504-512.
Wang et al., "Mutational Analysis of the Tyrosine Phosphatome in Colorectal Cancers," Science 2004;304:1164-6.
Xi et al., "Decreased STAT1 Expression by Promoter Methylation in Squamous Cell Carcinogenesis," J Natl Cancer Inst. 2006;98(3):181-9.
Xi et al., "In vivo antitumor efficacy of STAT3 blockade using a transcription factor decoy approach: implications for cancer therapy," Oncogene. 2005;24(6):970-9.
Youn et al., "Identifying cancer driver genes in tumor genome sequencing studies," Bioinformatics 2011;27(2):175-181.
Zhang et al., "Identification of STAT3 as a substrate of receptor protein tyrosine phosphatase T," Proc Natl Acad Sci USA 2007;104(10):4060-4.
Zhao et al., "Identification and functional characterization of paxillin as a target of protein tyrosine phosphatase receptor T," Proc Natl Acad Sci USA 2010;107(6):2592-7.

* cited by examiner

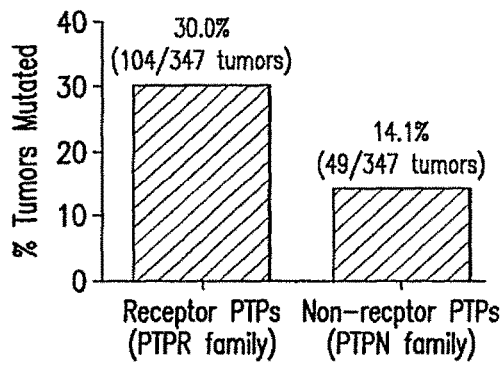
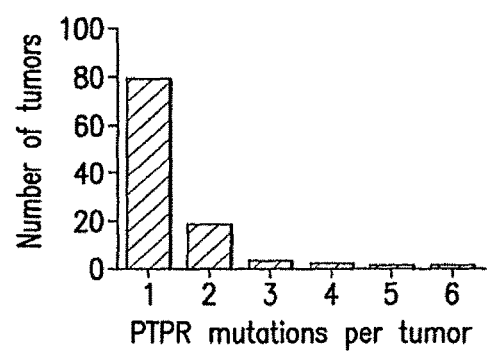
FIG. 7A
FIG. 7B
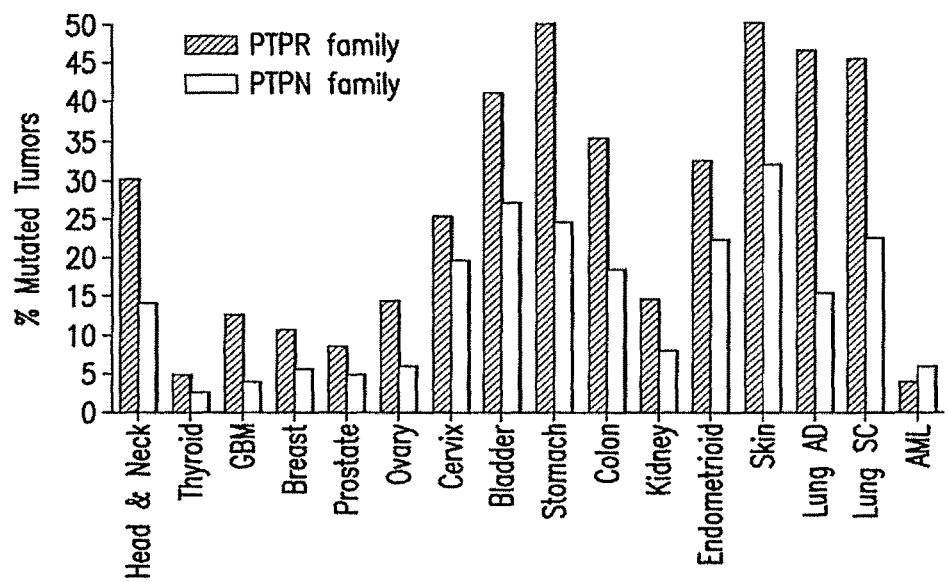
FIG. 7C

FUNCTIONAL GENOMICS SCREENING PLATFORM FOR HEAD AND NECK CANCER

PRIORITY CLAIM

This application is a continuation of PCT/US13/051866, filed Jul. 24, 2013, and which claims priority to U.S. Provisional Application No. 61/675,667, filed Jul. 25, 2012, to both of which priority is claimed and the contents of which are hereby incorporated by reference in their entireties herein.

GRANT SUPPORT

This invention was made with government support under Grant No. CA097190 awarded by the National Institutes of Health/National Cancer Institute. The government has certain rights in the invention.

1. INTRODUCTION

The present invention relates to human papillomavirus (HPV)-positive as well as HPV-negative screening platforms that are highly serum-dependent, for use as head and neck squamous cell carcinoma models.

2. BACKGROUND OF THE INVENTION

2.1. Driver Versus Passenger Mutations

The mutational landscape of head and neck squamous cell carcinomas (HNSCC) was recently reported (Stransky et al, Science, 2011). It was found that each HNSCC tumor contains a mean of 130 somatic mutations. It is speculated that most of the mutations detected are "passenger" events and do not represent oncogenic "driver" mutations. To date, identification of mutations that "drive" oncogenesis ("driver" mutations) has been accomplished by use of the IL-3-dependent Ba/F3 lymphoid cell model where introduction of putative oncogenic mutations confers survival in the absence of IL-3 (as IL-3 serves as the survival factor for Ba/F3 cells). Given that the factor-dependent Ba/F3 cells are a murine hematopoietic cell line with limited relevance in squamous cell carcinomas, it would be desirable to develop a HNSCC functional screening platform to identify "driver" mutations.

2.1. Receptor Protein Tyrosine Phosphatases

Phosphorylation and dephosphorylation of tyrosine residues on signaling proteins is coordinately regulated by protein tyrosine kinases and phosphatases. Mutation of these enzymes can lead to signaling dysregulation, uncontrolled cell growth and cancer formation. While activating mutations of tyrosine kinases have been well studied (Groesser et al., Mat. Genetics, 2012; Paez et al., Science, 2004) cancer-associated mutations of tyrosine phosphatases are incompletely understood. Select protein tyrosine phosphatases, receptor type (PTPRs) and non receptor type (PTPNs), function as tumor suppressor genes where gene mutation, deletion, or methylation have been reported to contribute to the cancer phenotype (Veeriah et al., 2009; Stransky et al., Science, 2011). In the human phosphatome, the PTPR family represents a major group of tyrosine phosphatases that mediate activation/deactivation of signaling pathways.

3. SUMMARY OF THE INVENTION

The present invention relates to HPV-positive as well as HPV-negative screening platforms that are highly serum-dependent, for use as HNSCC models. These HNSCC models die reproducibly in serum-deprived conditions and the introduction of driver mutations (or increased levels of the WT gene) confers enhanced cell survival and proliferation under serum deprivation. These platforms have the major advantages of allowing functional screening of mutations in relevant HNSCC models (HPV-positive and HPV-negative). In addition to oncogene screening, this model can also be used in drug discovery. Specifically, cells expressing mutations that confer increased survival can then be screened against panels of therapeutic agents to determine if the mutation(s) can predict the optimal treatment for patients whose tumors harbor the mutation(s).

4. BRIEF DESCRIPTION OF THE FIGURES

Figure 1B:
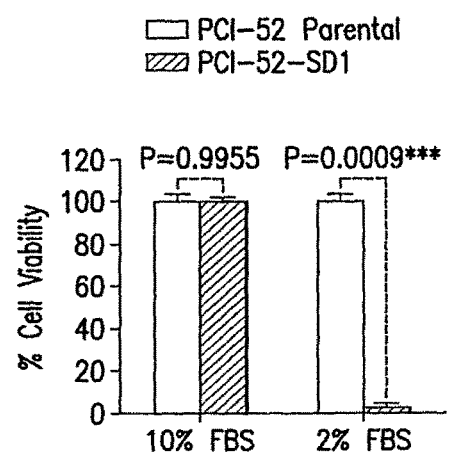

FIG. 1A-B. Creation of serum dependent HPV-positive and HPV-negative HNSCC driver mutation screening platforms. The serum-dependent (SD) sublines were developed upon initial screening of a total of 17 HNSCC cell lines, followed by isolation of sublines that are highly dependent on serum for survival (i.e., preferentially die in low or no serum conditions compared to the respective parental cells). (A) The HPV-positive UM-SCC47-SD17 subline is more dependent on serum for survival than its parental UM-SCC47 cell line (n=4). Cell viability was measured by MTT assay under serum-deprivation conditions. (B) The HPV-negative PCI-52-SD1 subline is more dependent on serum for survival than its parental PCI-52 cell line (n>6). Cell growth/survival was measured by MTT assay under serum deprivation conditions.

FIG. 2A-D. Expression of PIK3CA(H1047R) mutation increases HNSCC cell growth and PI3K signaling in the HPV-positive (UM-SCC47) and HPV-negative (PCI-52) HNSCC driver screening platforms. Growth of HPV+SD (A) and HPV(−)SD (B) cells expressing PIK3CA wildtype (WT) or PIK3CA(H1047R) mutant genes under serum-deprivation conditions, compared to the EGFP vector control (n=3). Expression of p110-α, p-AKT (S473) and p-AKT (T308) and total AKT were detected by Western blotting. Beta-tubulin was used as a loading and normalization control for densitometry calculations (numbers below each lane were normalized to β-tubulin level) for (C) HPV+SD (C) and HPV(−)SD (D) models.

Figure 3:
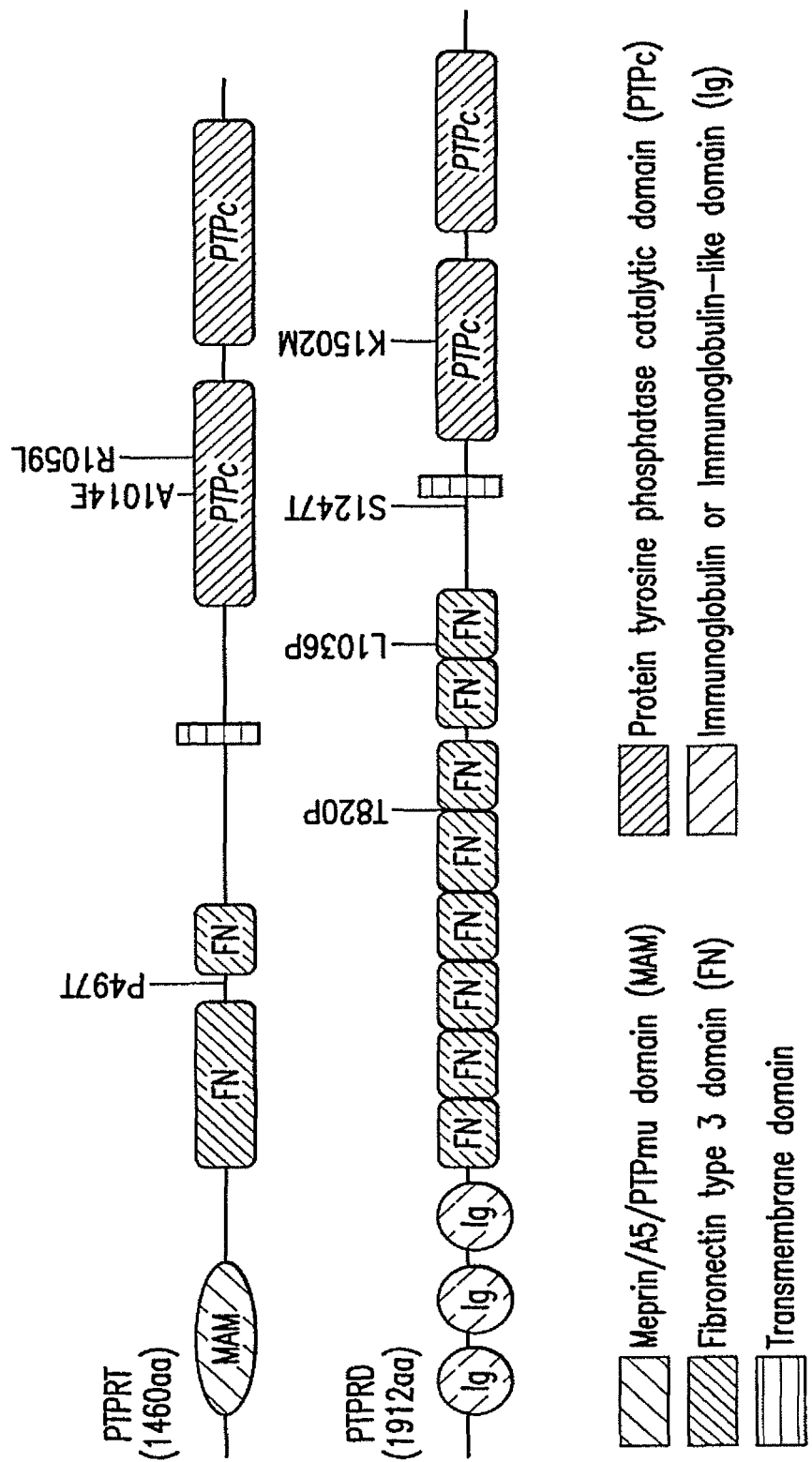

FIG. 3. PTPRT and PTPRD mutations in HNSCC.

Figure 4B:
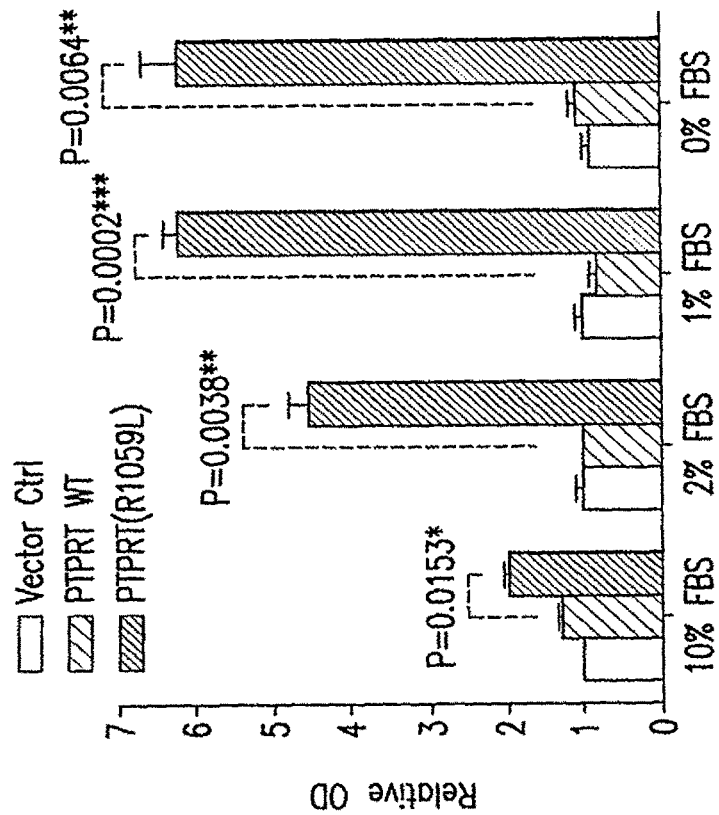
Figure 4A:
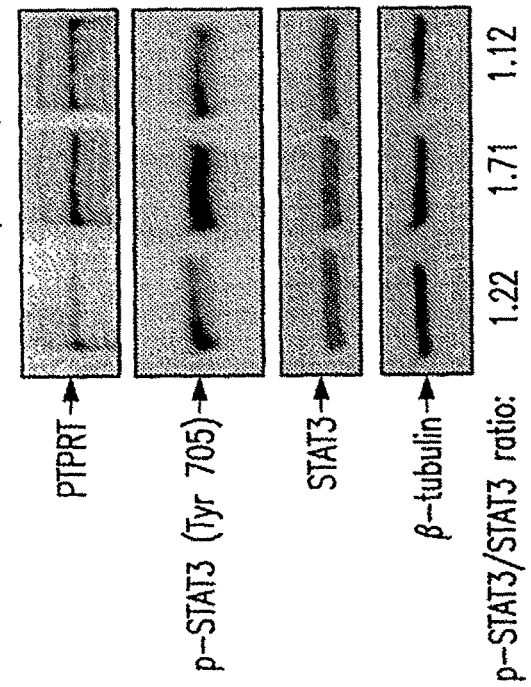

FIG. 4A-B. Mutation of PTPRT (R1059L) leads to increased STAT3 activation and cell survival/proliferation in PCI-52-SD1 cells. (A) PCI-52-SD1 cells were infected with retrovirus expressing the PTPRT(R1059L) mutant gene or PTPRT wildtype (WT) versus vector control (pMXs-EGFP vector) and gene expression was confirmed by Western blotting. Expression of PTPRT(R1059L) increases pSTAT3 expression. (B) PTPRT(R1059L) mutant-expressing HNSCC cells (PCI-52-SD1 cells by retrovirus infection) demonstrated increased survival/proliferation (vs PTPRT WT-expressing cells) upon serum withdrawal (n=3). Relative OD was determined by MTT assay.

Figure 5:
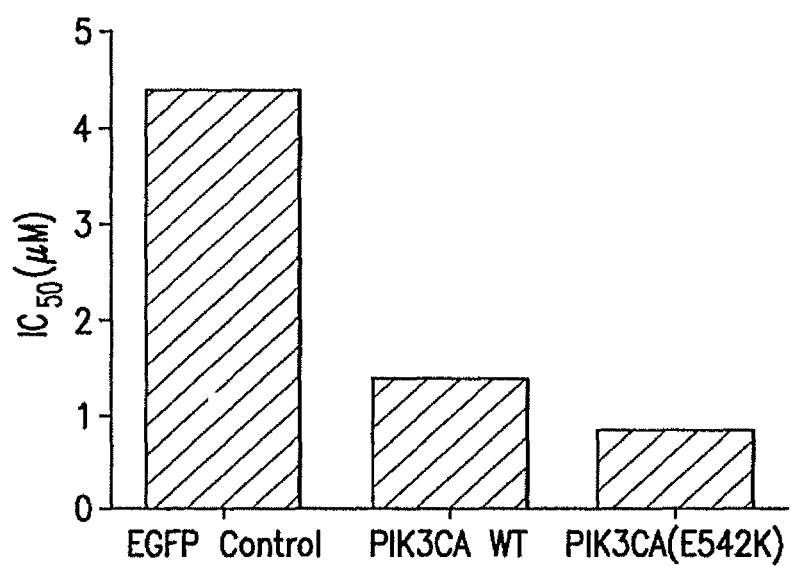

FIG. 5. PIK3CA mutation enhances sensitivity to PI3K pathway inhibition. Retrovirus-infected UMSCC-47 cells expressing control EGFP gene, PIK3CA (WT) or PIK3CA (E542K) mutant were subjected to BEZ-235 (from 0 to 10 μM) treatment for 72 h followed by growth determinations.

Figure 6:
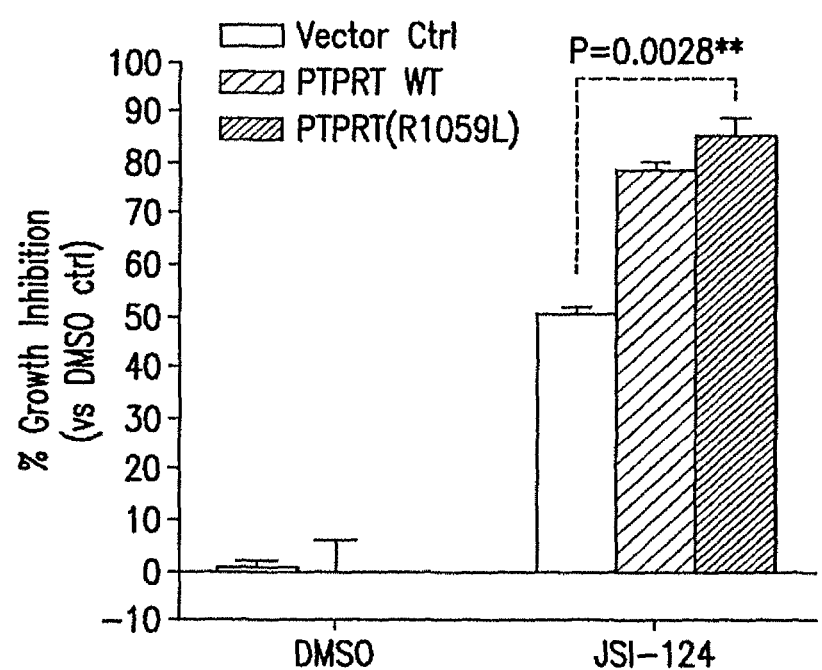

FIG. 6. Mutation of PTPRT(R1059L) leads to increased sensitivity to STAT3 inhibition in PCI-52-SD1 cells. PCI-52-SD1 cells were infected with retrovirus expressing the PTPRT(R1059L) mutant gene or PTPRT wildtype (WT) versus vector control (pMXs-EGFP vector). PTPRT (R1059L) expressing cells were more sensitive to growth inhibition following 24 hours of treatment with a preclinical JAK/STAT inhibitor, JSI-124, than vector control cells (n=4).

FIG. 7A-D. Whole-exome sequencing data of human cancers demonstrates a high rate of PTPR mutations. (A) Frequencies of PTPR (the receptor subtype) and PTPN (non-receptor subtype) somatic mutations in 347 HNSCC tumors. (B) A subset (104 cases, 30.0%, with PTPR mutations) of HNSCC tumors harbor mutations of multiple PTPRs. (C) The PTPR family is mutated at a higher rate than the PTPN family across human cancers. Data extracted from cBio portal (Cerami et al., Cancer Discovery, 2012). (D) Mutation and domain-mapping of all 3 most frequent mutated PTPR members in HNSCC. Percent tumors harboring PTPR mutations at the fibronectin III domain (FN3) and the phosphatase (PTPase) domain are indicated. Domains in PTPRs are defined according to the Swiss-Prot entries in Protein Knowledgebase (UniProtKB).

FIG. 8A-G. PTPRT mutations in HNSCC. (A) Serum-dependent PCI-52-SD1 cells stably expressing EGFP, wt PTPRT, or PTPRT (R1040L) mutant were assessed by MTT assay (n=4) for cell growth in the absence of serum. B) Structure of PTPRT PTPase domain 1 in complex with phosphotyrosine (p-Tyr, in green) of substrate (e.g. pSTAT3). The surface involved in the interaction with partner (p-Tyr-containing) protein is divided into three regions, residues within 0-5 Å from p-Tyr (red), 5-12 Å (purple), 12-25 Å (cyan). Positions found to be mutated in human cancers are indicated by "c"; trapping mutations by "Δ" 4; other experimentally verified loss-of-function mutations by "e" (Wang et al., Science, 2004; Lim et al, EMBO J., 2009). (C) Detailed view of the catalytic site. The largest part of the catalytic site is formed by the loop region starting from the catalytic C1084 until G1092 of the PTPase domain 1 of PTPRT. Positively charged R1090 and K996 are involved in the electrostatic interaction with the negatively charged phosphate group of p-Tyr. The aromatic part of p-Tyr is further stabilized by hydrophobic interactions with Y918 and I921. (D) Structure of the PTPase domain 2 of PTPRT in complex with p-Tyr (green) of the binding partner (e.g., phosphorylated STAT3). Annotations are as in panel B. Potential trapping mutations based on homology with domain 1 are indicated by "Δ". (E) Detailed view of the catalytic site. F) Stable expression of wt PTPRT reduced basal pSTAT3(Tyr705) in PCI-52-SD1 cells. (G) Effects of a PTPRT PTPase domain mutant PTPRT(R1040L) on phospho-STAT3 in HNSCC cells. PCI-52-SD1, were retrovirally transduced with vector encoding EGFP (vector control), WT PTPRT, or mutant PTPRT. Expression was detected by immunoblotting.

FIG. 9A-D. Schematics showing the location of mutations of human PTPR family members. All PTPRs are defined according to the Swiss-Prot entries in Protein Knowledgebase (UniProtKB).

Figure 10:
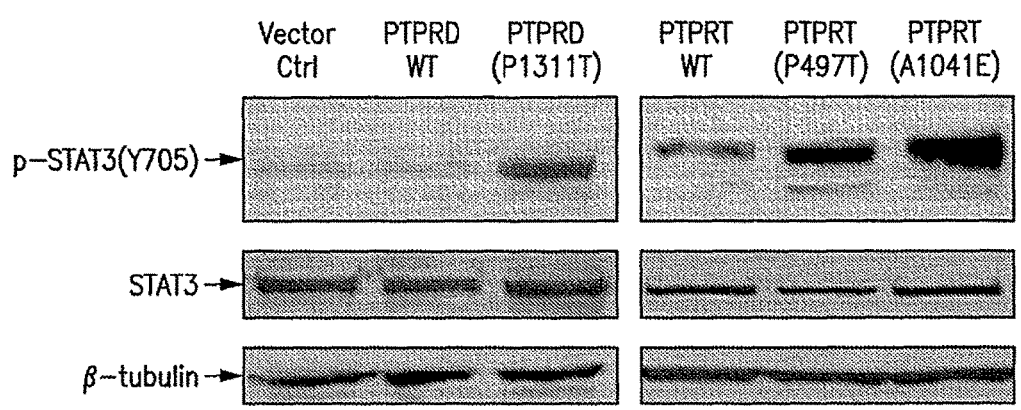

FIG. 10. HNSCC cells were transiently transfected with a PTPRD mutant, PTPRD (P1311T), a representative extracellular domain mutation of PTPRT, PTPRT (P497T), and another PTPase-domain mutation, PTPRT (A1041E). Expression levels of phospho-STAT3 (Tyr705) were detected by Western blotting. All three mutants showed elevated phospho-STAT3 (Tyr705) expression.

Figure 11:
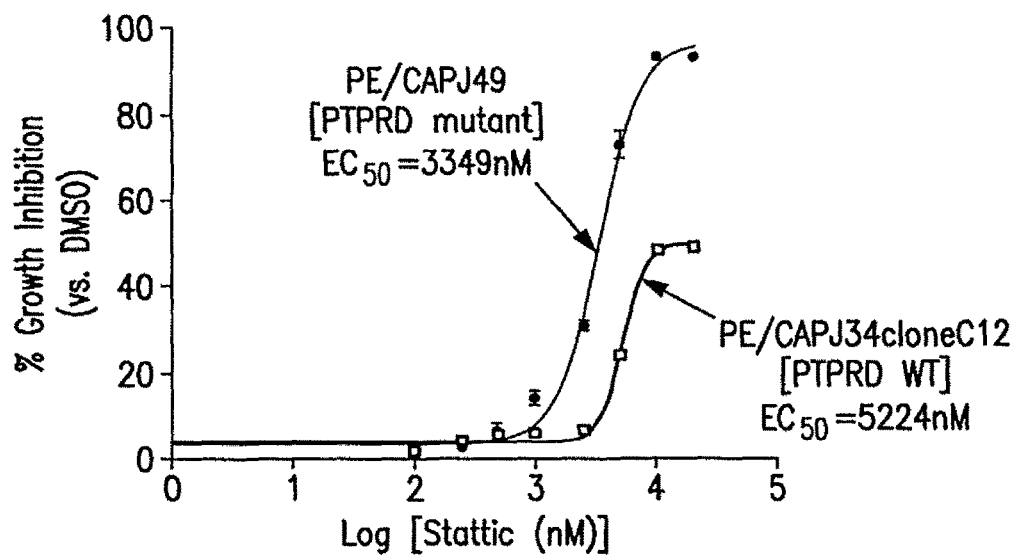
Figure 11:
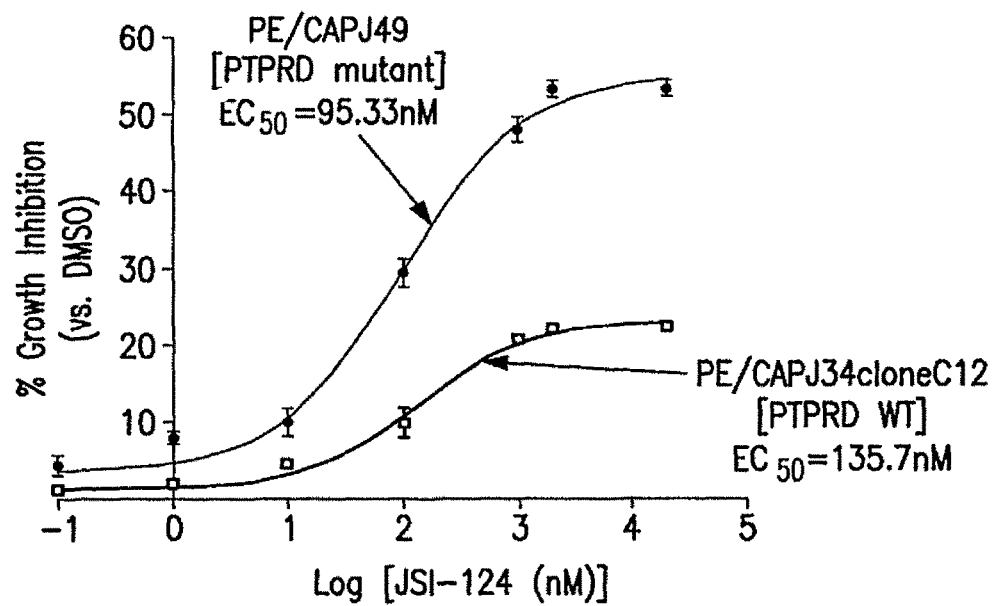

FIG. 11. HNSCC cells with an endogenous PTPRD phosphatase domain mutation (PE/CAPJ49, I1821V) are more sensitive to STAT3 pathways inhibitors (Stattic and JSI-124) compared to HNSCC cells with WT PTPRD (PE/CAPJ34 CloneC12).

Figure 12A:
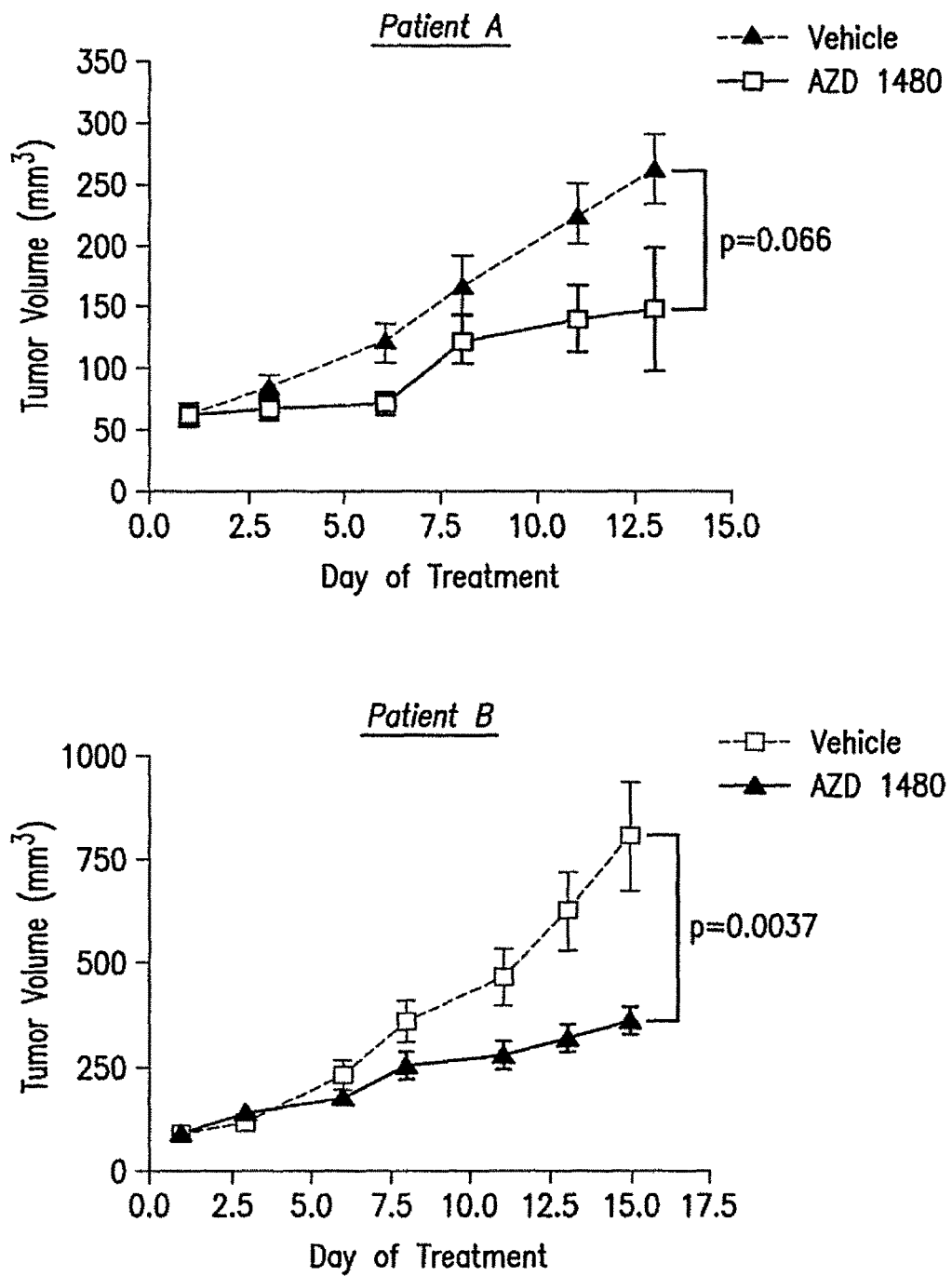
Figure 12B:
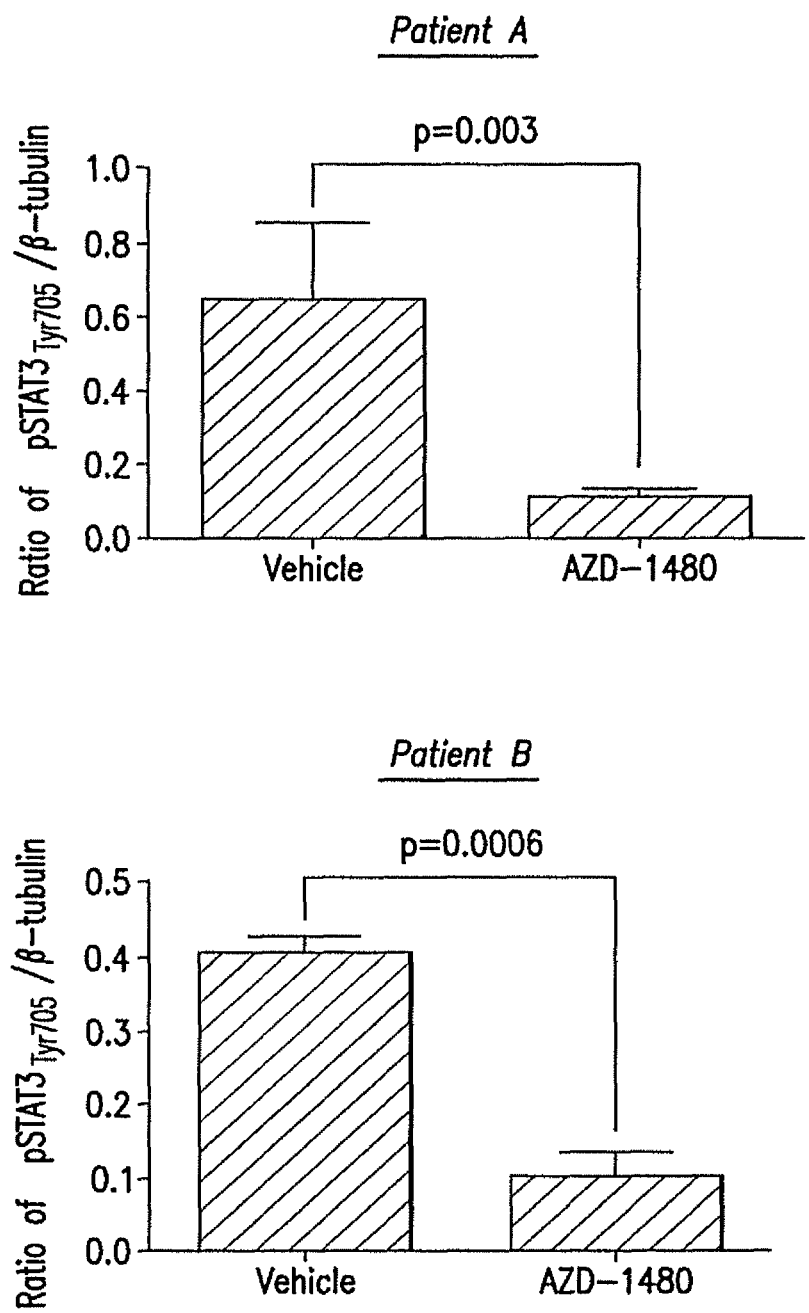

FIG. 12A-B. AZD1480 inhibits HNSCC patient tumor-graft growth in conjunction with reduce pSTAT3 expression. (A) Mice bearing heterotropic HNSCC patient tumorgrafts derived from 2 patients (10 mice per group) were treated with AZD1480 (30 mg/kg) or vehicle control, twice daily by oral gavage. Tumor volumes were measures every other day. Statistical difference was determined at the end of the experiment using the Mann-Whitney two-tailed test. (B) Tumors were harvested at the end of treatment, and whole cell lysates were prepared and subjected to immunoblotting with pSTAT3 (Tyr705) and STAT3 antibody. Beta-tubulin was used to assess protein loading. Densitometry was performed and bar graphs illustrate the cumulative findings from each HNSCC tumorgraph experiment.

Figure 13:
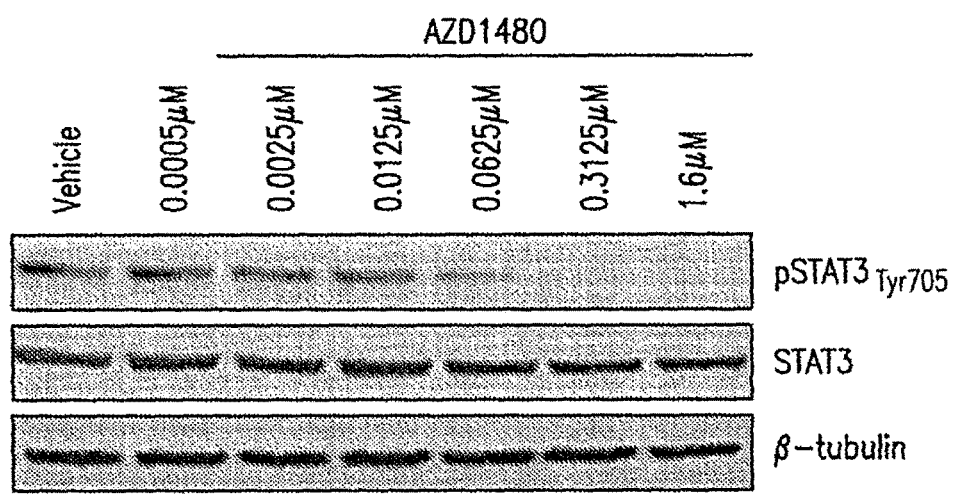

FIG. 13. ADZ1480 inhibits pSTAT3 in a dose dependent manner in a HNSCC cell line. UMSCC-1 cells were treated with increasing concentration of AZD1480. After 24 hours, cells were harvested to obtain cell lysates. Forty micrograms of protein/lane were subjected to electrophoresis and immunoblotted for phosphor-STAT3 (Tyr705) and total STAT3. Beta-tubulin was used as a loading control.

Figure 14:
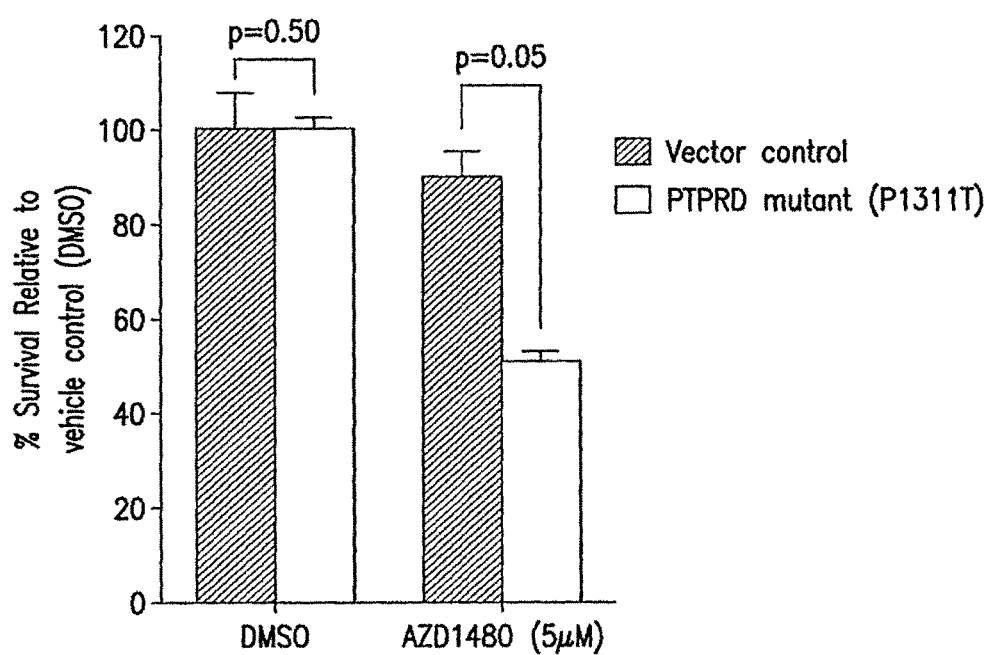

FIG. 14. Expression of a PTPRT mutant in HNSCC cells confer higher sensitivity to AZD1480. UM-SCC1 cells expressing mutant PTPRD (P1311T) or vector control were treated with AZD1480 (5 μm) or DMSO (vehicle) followed by MTT assay to determine % survival relative to vehicle control. Results are mean±SEM, performed in triplicate.

Figure 15B:
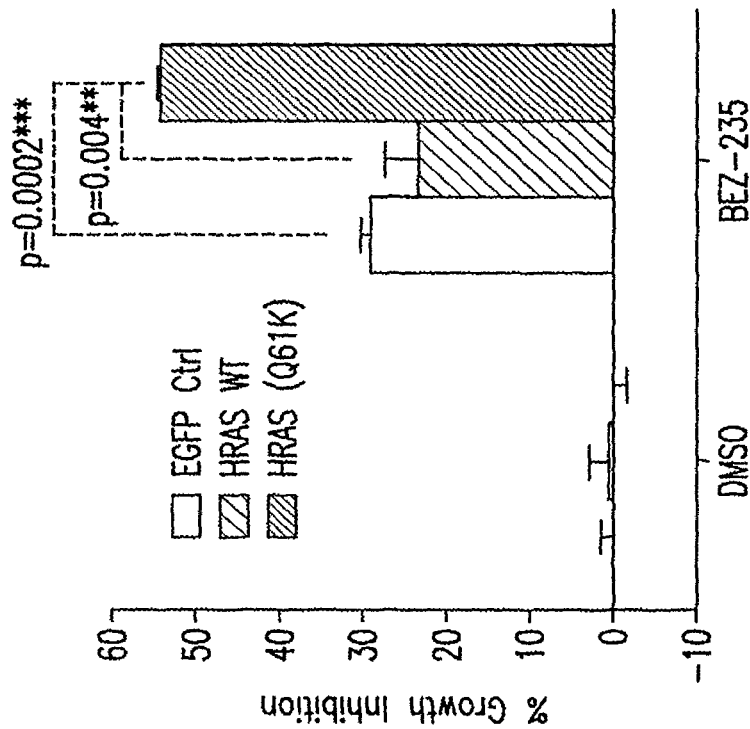
Figure 15A:
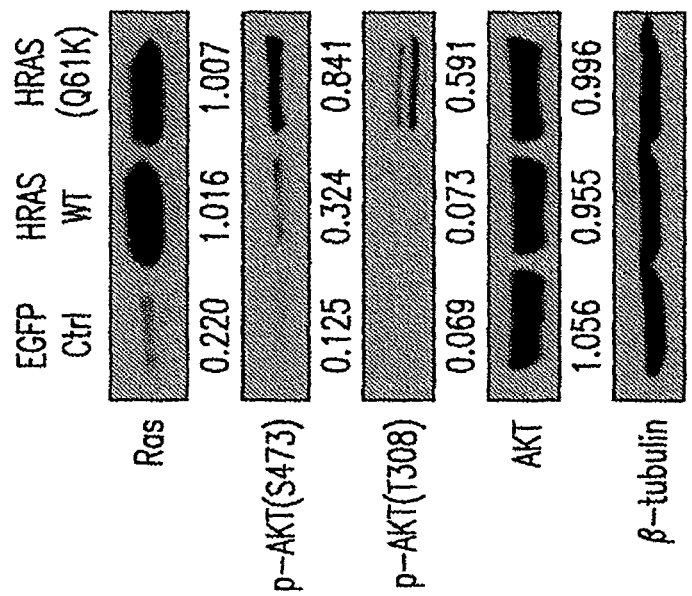

FIG. 15A-B. Activation of AKT by HRAS (Q61K) mutation in HNSCC cells confers sensitivity to a mTOR/PI3K inhibitor. (A) HRAS wildtype (WT) and HRAS (Q61K) mutant or an EGFP vector control was introduced into the HPV-HSNCC cell line, UM-SCC47, by retroviral infection. Expression of Ras, p-AKT (S473) and p-AKT(T308) and total AKT were detected by Western blotting. Beta-tubulin was used as a loading control for densitometry calculations (numbers below each lane). (B) UM-SCC47 cells expressing the HRAS(Q61K) mutant are more sensitive to growth inhibition induced by BEZ-235 (250 nM, 24 hours) when compared to the HRAS WT and EGFP vector control cells (n=4).

5. DETAILED DESCRIPTION OF THE INVENTION

For clarity and not by way of limitation, this detailed description is divided into the following subsections:
(i) Cell lines;
(ii) Methods of use; and
(iii) Kits.

5.1 Cell Lines

The present invention relates to HPV-positive (e.g., UM-SCC47) as well as HPV-negative (e.g., PCI-52) screening platforms that are highly serum-dependent, for use as HNSCC models (see, for example, FIGS. 1A and 1B, respectively). These HNSCC models die reproducibly in serum-deprived conditions and the introduction of one or more driver mutations (or increased levels of the WT gene) confers enhanced cell survival and proliferation under serum deprivation. These platforms have the major advantages of allowing functional screening of mutations in relevant HNSCC models (HPV-positive and HPV-negative).

HPV-positive HNSCC cells that have normal serum dependence are referred to herein by the designation HPV+-NS. HPV-positive HNSCC cells that are serum dependent are referred to herein by the designation HPV+SD. HPV-negative HNSCC cells that have normal serum dependence are referred to herein by the designation HPV(−)-NS. HPV-negative HNSCC cells that are serum dependent are referred to herein by the designation HPV(−)SD.

Accordingly, in certain non-limiting embodiments, the present invention provides for a serum-dependent cell line derived from a parent tumor cell line that is not serum dependent by selection for a cell that shows slower growth and/or lower survival at lower serum concentrations ("low-serum conditions"). As one non-limiting example, such cell is a member of a cloned population of cells. As one non-limiting example, the serum-dependent cell line shows a slower growth rate at 0%, 1%, 2%, and/or 5% serum (the foregoing being examples of "low serum conditions") relative to 10% serum. In certain non-limiting embodiments, the serum-dependent cell line, cultured in low serum conditions, has a growth rate which is up to 5 percent or up to 10 percent or up to 15 percent or up to 20 percent or up to 25 percent or up to 30 percent of the growth rate of the serum-dependent cell line at 10% serum.

In one non-limiting embodiment, the parent tumor cell line is a human tumor cell line. As one non-limiting example, the parent tumor cell line is a human HNSCC cell line. In certain non-limiting embodiments, the serum-dependent cell is clonally derived from the parent tumor cell line. For example, a serum-dependent cell line can be prepared by plating the parental tumor cell line as single cells to grow as single clones, where the single clones were subjected to low serum conditions (e.g., 0%, 1%, 2%, or 5% serum versus 10% serum) for 1-2 weeks followed by the assessment of cell growth.

In one non-limiting embodiment, the parent tumor cell line is a human HNSCC cell line that is HPV+. In certain non-limiting embodiments, the HNSCC cell line that is HPV(+) is selected from the group consisting of UD-SCC-2, UPCI:SCC90, UM-SCC47, or 93-VU-147T. As one non-limiting example, the HNSCC cell line that is HPV(+) is UM-SCC47. As one non-limiting example, the HPV+SD cell line is UM-SCC47-SD-17.

In certain non-limiting embodiments, the parent tumor cell line is a human HNSCC cell line that is HPV(−). As certain non-limiting embodiments, the HNSCC cell line that is HPV(−) is selected from the group consisting of PCI-13, PCI-30 and PCI-52. As one non-limiting example, the human HNSCC cell line that is HPV(−) is PCI-52. As one non-limiting example, the HPV(−) SD cell line is PCI-52-SD1.

In certain non-limiting embodiments, a cell of a serum-dependent cell line prepared from a HNSCC cell line, as described above, may carry an introduced driver gene/mutation (for example, introduced via a vector, such as a retrovirus or other means known in the art). In non-limiting embodiments, the introduced driver gene/mutation is stably expressed. In a non-limiting embodiment, the driver gene/mutation is transiently expressed. In a non-limiting embodiment, a cell of a serum-dependent cell line prepared from a HNSCC cell line may carry one or more driver genes and/or mutations.

In a non-limiting embodiment, the cell of a serum-dependent cell line prepared from a HNSCC cell line may carry one or more driver genes/mutations and one or more passenger genes/mutations. Non limiting examples of passenger mutations include, but are not limited to, mutations in Caspase 11 and ENO1.

In non-limiting embodiments, the one or more driver genes/mutations is a wild-type or mutated form of a gene that functions in the following signaling pathways: the JAK/STAT signaling pathway, the MAPK pathway, the PI3K signaling pathway, or a combination thereof.

In non-limiting embodiments, the one or more driver genes/mutations is a wild-type or mutated form of a PTPR or a PTPN family member and a wild-type or mutated form of one or more genes that function in the following signaling pathways: the JAK/STAT signaling pathway, the MAPK pathway, the PI3K signaling pathway, or a combination thereof.

In non-limiting embodiments, the one or more driver genes/mutations is selected from the mutations and genes set forth in TABLES 1 and 2 and FIGS. 7 and 9.

In non-limiting embodiments, the one or more driver genes/mutations is a wild-type or mutated gene selected from the group consisting of JAK1, JAK2, JAK3, STAT1, STAT2, STAT3, STAT4, STAT5A, STAT5B, STAT6, SOCS3, SHP2, IL6ST, IL6R, IL6, or a combination thereof. In one non-limiting embodiment, the driver gene/mutation is a wild-type or mutant form of STAT3. In one non-limiting embodiment, the driver gene/mutation is STAT3 (E63D). In one non-limiting embodiment, the driver gene/mutation is a wild-type or mutant form of STAT1. In one non-limiting embodiment, the driver gene/mutation is STAT1 (Q330K).

In non-limiting embodiments, the one or more driver genes/mutations is a wild-type or mutated gene selected from the group consisting of ERK1, ERK2, MEK1, MEK2, RAF1, ARAF, BRAF, HRAS, KRAS, NRAS, SHC1, SHC2, SHC3, GRB2, or a combination thereof. In one non-limiting embodiment, the driver gene/mutation is a wild-type or mutant form of HRAS. In one non-limiting embodiment, the driver gene/mutation is HRAS (Q61K).

In non-limiting embodiments, the one or more driver genes/mutations is a wild-type or mutated gene selected from the group consisting of PIK3CA, PIK3AP1, PIK3C2A, PIK3C2B, PIK3C2G, PIK3CB, PIK3CD, PIK3CG, PIK3IP1, PIK3R1/2/3/4/5/6, AKT1/2/3, MTOR, PTEN, PDK1, TSC1/2, RICTOR, RPTOR, or a combination thereof. In one non-limiting embodiment, the one or more driver gene/mutation is a wild-type or mutant form of PIK3CA. In non-limiting embodiments, the one or more driver gene/mutation is PIK3CA (Wild-type), PIK3CA (H1047R), PIK3CA (E542K), PIK3CA (H1047L), PIK3CA (E545K), PIK3CA (R115L), PIK3CA (G363A), PIK3CA (C971R), or PIK3CA (R975S).

In non-limiting embodiments, the one or more driver genes/mutations is selected from the group consisting of the wild-type and mutant forms of PTPRA, PTPRB, PTPRF, PTPRG, PTPRH, PTPRJ, PTPRK, PTPRM, PTPRN, PTPRN2, PTPRO, PTPRR, PTPRS, PTPRU, PTPRZ1, or a combination thereof. In non-limiting embodiments, the driver gene/mutation can be PTPRT (R1059L), PTPRT (A1022E), PTPRT (P497T), PTPRT (A1041E), PTPRT (R1040L), PTPRD (I1821V), PTPRD (P1311T), PTPRD (T820P), PTPRD (L1036P), PTPRD (S1247T), PTPRD (K1502M), or a combination thereof.

In non-limiting embodiments, the one or more driver genes/mutations is selected from the group consisting of the wild-type and mutant forms of PTPN1, PTPN2, PTPN3, PTPN4, PTPN5, PTPN6, PTPN7, PTPN9, PTPN11, PTPN12, PTPN13, PTPN14, PTPN18, PTPN20A, PTPN20B, PTPN21, PTPN22, PTPN23, or a combination thereof.

In non-limiting embodiments, the one or more driver genes/mutations is selected from the group consisting of the wild-type and mutant forms of PIK3C2G, PTEN, PIK3R1, MTOR, PIK3CA, PIK3CG, PIK3IP1, PIK3AP1, PIK3R5, TSC2, AKT2, JAK3, STAT1, or a combination thereof. In non-limiting embodiments, the one or more driver genes/mutations is selected from the group consisting of PIK3C2G, PIK3C2G (V656L), PIK3C2G (S1272L), PTEN (WT), PTEN (D92E), PTEN (R335Stop), PTEN (R14S), PIK3R1 (WT), PIK3R1 (D560H), MTOR, MTOR (L2260H), MTOR (R1161Q), PIK3CA (WT), PIK3CA (H1047L), PIK3CA (E545K), PIK3CA (E542K), PIK3CA (H1047R), PIK3CG (WT), PIK3CG (G491E), PIK3CG (A156V), PIK3IP1 (WT), PIK3IP1 (WT), PIK3IP1 (A144S), PIK3AP1 (WT), PIK3AP1 (G313R), PIK3R5 (WT), PIK3R5 (E322K), PIK3R5 (E60Stop), TSC2 (WT), TSC2 (S1514Stop), AKT2 (WT), AKT2 (Y351C), JAK3 (WT), JAK3 (R948C), STAT1 (WT), STAT1 (Q330K), or a combination thereof.

In certain non-limiting embodiments, the driver gene/mutation can be introduced into the serum-dependent cell via any method known in the art. Non-limiting methods of introducing the driver gene/mutation include, but are not limited to, calcium phosphate transfection, Lipofectamine transfection, Fugene transfection, microinjection, or electroporation. In a non-limiting embodiment, the driver gene/mutation can be introduced by a vector. Non-limiting examples of vectors include, but are not limited to, plasmids, cosmids, artificial chromosomes and may include, for example, pMXs-Puro (Cell Biolabs, Inc., San Diego, Calif.), pKK plasmids (Clonetech), pUC plasmids, pET plasmids (Novagen, Inc., Madison, Wis.), pRSET plasmids (Invitrogen, San Diego, Calif.), pCDNA3 plasmids (Invitrogen), pREP plasmids (Invitrogen), or pMAL plasmids (New England Biolabs, Beverly, Mass.). Additional non-limiting examples of vectors include, but are not limited to, viruses, such as adenoviruses, adeno-associated virus (AAV), vaccinia, herpesviruses, baculoviruses and retroviruses, parvovirus, lentivirus, bacteriophages, cosmids, plasmids, fungal vectors, naked DNA, DNA lipid complexes, and other recombination vehicles typically used in the art.

In certain non-limiting examples, the vector may be introduced into at least 5%, at least 10%, at least 20%, at least 25%, at least 300/%, at least 35%, at least 40%, at least 44%, at least 50%, at least 57%, at least 62%, at least 70%, at least 74%, at least 75%, at least 80%, or at least 90% of the total population of cells. In a certain non-limiting embodiment, a single vector may comprise two or more driver genes/mutations.

Recombinant cloning vectors often include one or more replication systems for cloning or expression, one or more markers for selection in the host cell, e.g., antibiotic resistance, and one or more expression cassettes. In non-limiting embodiments, the vectors to be used in the present invention may comprise expression control sequences such as constitutive or conditional promoters. For example, suitable promoters include, but are not limited to, CMV, HSVI-TK, SV40, EF-1α, β-actin, PGK, and inducible promoters, such as those containing Tet-operator elements. In certain non-limiting embodiments, the promoter can be inducible, temperature regulated, tissue specific, repressible, heat-shock, developmental, cell lineage specific, eukaryotic, prokaryotic, or temporal promoters.

In certain non-limiting embodiments, the vector further comprises a marker gene or a tag sequence that facilitates identification or selection of cells that have been transfected or infected. Non-limiting examples of a tag or marker include, but are not limited to, a HIS tag, a myc tag, a hemagglutinin (HA) tag, protein C, VSV-G, FLU, FLAG, BCCP, maltose binding tag, Nus-tag, thioredoxin, Strep-tag, S-tag, VS, TAP, or CBP, or fluorescent protein genes, e.g., EGFP, DS-Red, YFP, and CFP.

5.2 Methods of Use

The cell of the present invention may be used to identify a driver gene/mutation for HNSCC by methods exemplified in the working example below. Accordingly, the present invention provides for a method of identifying a driver gene or mutation in a cancer comprising inserting a putative driver gene/mutation into a cell of a serum dependent tumor cell line (as described above) and then determining the ability (e.g., growth rate) of the cell containing the putative driver gene/mutation to grow under serum depleted conditions, where if the cell is able to grow at an improved rate and/or exhibit improved survival under serum depleted conditions relative to a cell of the serum dependent tumor cell line lacking the putative driver gene/mutation indicates that the putative driver gene/mutation is a driver gene/mutation.

In certain non-limiting embodiments, the driver gene/mutation can be introduced into the serum-dependent cell via any method known in the art, as described above.

In a non-limiting embodiment, growth rate, cell death, proliferation, and/or survival may be assayed to determine if a putative driver gene/mutation is a driver gene/mutation.

In certain non-limiting embodiments, at least a 2-fold, 3-fold, 4-fold, 5-fold, 6-fold, or 7-fold increase in the relative survival, at low serum conditions, of a cell of a serum dependent tumor cell line expressing a putative driver gene/mutation compared with a cell of a serum dependent tumor cell line lacking the putative driver gene/mutation indicates that the putative driver gene/mutation is a driver gene/mutation.

In certain non-limiting embodiments, at least a 2-fold, 3-fold, 4-fold, 5-fold, 6-fold, or 7-fold increase in the relative growth rate and/or proliferation, at low serum conditions, of a cell of a serum dependent tumor cell line expressing a putative driver gene/mutation compared with a cell of a serum dependent tumor cell line lacking the putative driver gene/mutation indicates that the putative driver gene/mutation is a driver gene/mutation.

In addition to oncogene or driver gene/mutation screening, this model can also be used in drug discovery or in optimizing individual patient therapy. Specifically, a tumor cell expressing a driver gene/mutation that confers increased survival and/or a higher growth rate at low serum conditions can then be screened against one or more therapeutic agent to determine which therapeutic agent(s) show(s) superior efficacy in inhibiting growth of the cell. In one non-limiting embodiment, the cell expressing a driver gene/mutation for such testing may be a serum dependent cell, for example a HPV+SD cell or HPV(−)SD cell derived from a HNSCC cell line, as described above.

In certain non-limiting embodiments, said cell to be used in screening one or more therapeutic agents may carry one or more wild-type or mutated forms of genes selected from the genes and mutations set forth in TABLES 1 and 2 and FIGS. 7 and 9.

In certain non-limiting embodiments, said cell, to be used in screening one or more therapeutic agents, may carry a wild-type gene or mutant gene selected from the following list: PIK3CA, including but not limited to the wild type gene or mutants PIK3CA (H1047R) or PIK3CA (E542K), and mutations of protein tyrosine phosphatase receptor types T and D (PTPRT and PTPRD), for example but not limited to PTPRT (R1059L) and PTPRD (P1311T).

In non-limiting embodiments, said cell, to be used in screening one or more therapeutic agents, may carry one or more wild-type genes or mutant genes selected from the following list: PIK3C2G, PTEN, PIK3R1, MTOR, PIK3CA, PIK3CG, PIK31P1, PIK3AP1, PIK3R5, TSC2, AKT2, JAK3, STAT1, or a combination thereof. In non-limiting embodiments, said cell, to be used in screening one or more therapeutic agents, may carry one or more driver genes/mutations selected from the group consisting of PIK3C2G, PIK3C2G (V656L), PIK3C2G (S1272L), PTEN (WT), PTEN (D92E), PTEN (R335Stop), PTEN (R14S), PIK3R1 (WT), PIK3R1 (D560H), MTOR, MTOR (L2260H), MTOR (R1161Q), PIK3CA (WT), PIK3CA (H1047L), PIK3CA (E545K), PIK3CA (E542K), PIK3CA (H1047R), PIK3CG (WT), PIK3CG (G491E), PIK3CG (A156V), PIK31P1 (WT), PIK31P1 (WT), PIK31P1 (A144S), PIK3AP1 (WT), PIK3AP1 (G313R), PIK3R5 (WT), PIK3R5 (E322K), PIK3R5 (E60Stop), TSC2 (WT), TSC2 (S1514Stop), AKT2 (WT), AKT2 (Y351C), JAK3 (WT), JAK3 (R948C), STAT1 (WT), STAT1 (Q330K), or a combination thereof.

In non-limiting embodiments, the potential therapeutic agents can be chemical moieties including small molecules, polypeptides, peptides, peptide mimetics, antibodies or antigen-binding portions thereof. In non-limiting embodiments, the antibodies may be non-human antibodies, chimeric antibodies, humanized antibodies, or fully human antibodies. In certain embodiments, the antibodies may be intact antibodies comprising a full complement of heavy and light chains or antigen-binding portions of any antibody, including antibody fragments (such as Fab, Fab', F(ab')2, Fd, Fv, dAb, and the like), single chain antibodies (scFv), single domain antibodies, all or an antigen-binding portion of a heavy chain or light chain variable region.

In certain non-limiting embodiments, the therapeutic agent can be a JAK/STAT signaling pathway inhibitor. Non-limiting examples of JAK/STAT signaling pathway inhibitors include, but are not limited to, Stattic (Sigma-Aldrich, MO), JSI-124 (Calbiochem, MA), Pyridone 6, Ruxolitinib (ICNB0182424, Novartis), and AZD1480 (AztraZeneca). In non-limiting embodiments, the therapeutic agent can be a STAT3 inhibitor, e.g., Stattic. In non-limiting embodiments, the therapeutic agent can be a JAK inhibitor, e.g., AZD1480. For example, a cell model of the present invention expressing a PTPRD mutation, PTPRD (P311T), demonstrated decreased survival when treated with AZD1480 compared to a cell model of the present invention expressing a control vector.

In non-limiting embodiments, the therapeutic agent can be a PI3 kinase inhibitor. Non-limiting examples of PI3 kinase inhibitors include, but are not limited to, BEZ-235 (Novartis) and BKM-120 (Novartis).

In certain non-limiting embodiments, the cell model of the present invention can be used to determine the appropriate doses of a therapeutic agent that will have a therapeutic effect on a patient. In certain non-limiting embodiments, the cell model of the present invention can be used to determine the appropriate doses of a PI3 kinase inhibitor that will result in tumor growth inhibition in a patient with HNSCC. In certain non-limiting embodiments, the cell model of the present invention can be used to determine the appropriate doses of a JAK/STAT signaling pathway inhibitor that will result in tumor growth inhibition in a patient with HNSCC. For example, the cell model of the present invention can be used to determine the appropriate doses of AZD1480 that will result in tumor growth inhibition in a patient with HNSCC. In certain embodiments, the cell model of the present invention can be used to determine the pharmacodynamic effects of a therapeutic agent.

In certain non-limiting embodiments, the cell model of the present invention can be used to identify genetic mutations that are associated with an enhanced response to a therapeutic drug, e.g., superior efficacy in inhibiting growth, compared to a cell model of the present invention that does not contain the identified genetic mutations. The identified mutations can be used as biomarkers to assist in determining which patient, based on the presence of the identified genetic mutation in the patient's tumor, will respond favorably and/or more favorably to treatment with the therapeutic agent. In certain non-limiting embodiments, the therapeutic agent can be Stattic, JSI-124, Pyridone 6, Ruxolitinib (ICNB0182424), AZD1480, BEZ-235, BKM-120, or a combination thereof.

In certain non-limiting embodiments, screening of therapeutic drugs may be performed with cells of the present invention that contain different driver genes/mutations to correlate specific mutations with therapeutic efficacy. In certain non-limiting embodiments, the application of a therapeutic agent to one or more cells, each expressing a different driver gene/mutation, can be performed to identify which driver gene/mutation increases sensitivity to the therapeutic agent. In certain embodiments, the method of identifying a driver gene or mutation that increases sensitivity to a therapeutic agent comprises applying a therapeutic agent to one or more cells, each of which expresses a different driver gene/mutation, and then determining the ability of the one or more cells to grow under low serum conditions, where if one cell that expresses a driver gene or mutation is able to grow at a reduced rate and/or exhibit reduced survival under low serum conditions in the presence of the therapeutic agent relative to a cell that expresses a different driver gene/mutation in the presence of the same therapeutic agent indicates that the driver gene/mutation that results in a reduced growth rate increases sensitivity to the therapeutic agent. Identification of driver gene/mutations that increase sensitivity to a therapeutic agent can be used as biomarkers to assist in optimizing individual patient therapy. For example, a specific driver gene/mutation which increases the effectiveness of the therapeutic drug in inhibiting growth compared to the effectiveness of the therapeutic agent on a cell expressing a different driver gene/mutation indicates that patient tumors that contain the driver gene/mutation that increases sensitivity to the therapeutic agent will be more responsive to treatment with the therapeutic drug.

Accordingly, in certain non-limiting embodiments the invention provides for a method of identifying a driver gene or mutation that increases sensitivity to a therapeutic agent comprising applying the therapeutic agent to one or more cells (which may be, for example, HNSCC cells that are serum dependent), each of which expresses a different driver gene/mutation, and then determining the ability of the one or more cell to grow under low serum conditions, where if one cell that expresses a first driver gene or mutation is able to grow at a reduced rate and/or exhibit reduced survival under low serum conditions in the presence of the therapeutic agent relative to a cell that expresses a different, second, driver gene/mutation in the presence of the same therapeutic agent, then the first driver gene/mutation is indicated to be associated with increased sensitivity to the therapeutic agent.

In certain non-limiting embodiments, the invention provides for a method of treating a cancer, for example HNSCC, in a subject, where if a cancer cell of the subject contains a driver gene/mutation associated with increased sensitivity to a therapeutic agent, then treating the subject with the therapeutic agent. The driver gene associated with increased sensitivity to the therapeutic agent may be determined as set forth above.

This model can also be used to determine whether a secondary agent increases sensitivity to a therapeutic drug. Specifically, a tumor cell expressing a driver gene/mutation that incurs increased survival under serum depleted conditions can be screened against one or more secondary agents in the presence of a therapeutic drug to determine which candidate secondary agent(s) enhances the efficacy of the therapeutic drug on its inhibition on the growth and/or survival of the cell, where if there is an enhanced reduction in the growth or survival in the presence of the candidate secondary agent relative to the growth or survival in the absence of the candidate secondary agent indicates that the candidate secondary agent increases the sensitivity of the cell to the therapeutic agent.

In certain non-limiting embodiments, the cell proliferation and/or the growth rate may be measured using any method known in the art including, but not limited to, assaying the DNA cell cycle, the 3H-thymidine incorporation method, the cell count method, optical density (e.g., OD 260 for DNA), the colorimetric cell proliferation assay, the efficiency of colony formation method, cell confluency, or combination thereof. Non-limiting examples of colorimetric cell proliferation assays include the WSTI cell proliferation assay (Cat No. 1 644 807 from Roche), MTT cell proliferation assay (BioPionneer) assay, XTT cell proliferation assay (BioPioneer) assay, the CellTiter-Glo assay, and calcein cell proliferation assay (Cat. No. QIA128 from Calbiochem).

In certain non-limiting embodiments, the effect a driver gene/mutation has on the proliferation of a tumor cell under low serum conditions can be further determined by performing one or more of the following assays, which include, but are not limited to, apoptosis multi-endpoint assays (Multi-endpoint apoptosis/necrosis kit, Invitrogen), migration assay, invasion assay, or in-vivo tumor assays, e.g., implantation of driver gene/mutation expressing cells into immunocompromised mice).

In certain non-limiting embodiments, the efficacy of a therapeutic agent can be evaluated by determining the $IC_{50}$ value for each therapeutic drug.

5.3 Kits

The present invention provides for kits for screening potential therapeutic agents using one or more cell lines of the invention. In certain non-limiting embodiments, a kit can include a HPV+SD cell or HPV(−)SD cell derived from a HNSCC cell line, as described above. In certain non-limiting embodiments, a kit can include the HPV(−) SD cell line PCI-52-SD1. In certain non-limiting embodiments, a kit can include the HPV+SD cell line UM-SCC47-SD-17. In certain non-limiting embodiments, a kit can include one or more cells of a serum dependent tumor cell line expressing one or more driver genes/mutations, as described above. The kit can further comprise a culture medium appropriate for maintaining the one or more cell lines.

In certain embodiments, a kit can include one or more cells of a serum dependent tumor cell line of the present invention and one or more vectors comprising a nucleic acid molecule encoding a driver gene/mutation.

In certain non-limiting embodiments, the kit may comprise a cell panel comprising at least 1, 2, 3, 4, 5, 6, 10, 15, 20, 25, 30, 35, 40, 50, or 100 cell samples, where each cell sample contains cells of the present invention that expresses the same driver gene/mutation. In certain non-limiting embodiments, the kit may comprise a cell panel comprising at least 1, 2, 3, 4, 5, 6, 10, 15, 20, 25, 30, 35, 40, 50, or 100 cell samples, where each cell sample, which contains cells of the present invention, expresses a different driver gene/mutation. In a non-limiting embodiment, the kit may be provided in a multi-well plate format, for example, in one or more 4, 6, 12, 24, 48, 72, 96, 384, or 1536 well plates.

TABLE 1

| | Ref. GenBank Seq. | Tumor | Mutation Type | Genomic Change | Allele Change | Amino Acid Change |
|---|---|---|---|---|---|---|
| PI3K Pathway Component | | | | | | |
| PIK3CA | NM_006218 | HN_62415 | Missense | g.chr3:178936092A > G | c.1791A > G | p.E545G |
| | | HN_62426 | Missense | g.chr3:178936091G > A | c.1790G > A | p.E545K |
| | | HN_62469 | Missense | g.chr3:178952085A > G | c.3297A > G | p.H1047R |
| | | HN_62825 | Missense | g.chr3:178916957G > T | c.501G > T | p.R115L |
| | | HN_63027 | Missense | g.chr3:178936082G > A | c.1781G > A | p.E542K |
| | | HN_63039 | Missense | g.chr3:178952085A > T | c.3297A > T | p.H1047L |
| | | 325 | Missense | g.chr3:180434779A > T | c.3297T > A | p.H1047L |
| | | HN11PT | Missense | g.chr3:180434779A > G | c.3140A > G | p.H1047R |
| | | HN41PT | Missense | g.chr3:180434779A > T | c.3140A > T | p.H1047L |
| | | HNPTS_1 | Missense | g.chr3:178936091G > A | c.1633G > A | p.E545K |
| | | HNPTS_14 | Missense | g.chr3:178922319G > C | c.1088G > C | p.G363A |
| | | HNPTS_20 | Missense | g.chr3:178948139T > C | c.2911T > C | p.C971R |
| | | HNPTS_25 | Missense | g.chr3:178952085A > G | c.3140A > G | p.H1047R |
| | | HNPTS_26 | Missense | g.chr3:178948153A > T | c.2925A > T | p.R975S |
| | | HNPTS_29 | Missense | g.chr3:178936082G > A | c.1624G > A | p.E542K |
| | | HNPTS_35 | Missense | g.chr3:178936082G > A | c.1624G > A | p.E542K |
| | | HNPTS_38 | Missense | g.chr3:178952085A > G | c.3140A > G | p.H1047R |
| | | HNPTS_42 | Missense | g.chr3:178936091G > A | c.1633G > A | p.E545K |
| | | HNPTS_43 | Missense | g.chr3:178952085A > G | c.3140A > G | p.H1047R |
| PIK3CG | NM_002649 | HN_01000 | Missense | g.chr7:106545584C > A | c.3146C > A | p.R1021S |
| | | HN_62532 | Missense | g.chr7:106520100T > A | c.2613T > A | p.L843H |

TABLE 1-continued

| | Ref. GenBank Seq. | Tumor | Mutation Type | Genomic Change | Allele Change | Amino Acid Change |
|---|---|---|---|---|---|---|
| | | HN_62854 | Missense | g.chr7:106509343C > T | c.1422C > T | p.S446F |
| | | HN_63021 | Missense | g.chr7:106509582C > T | c.1661C > T | p.P526S |
| | | HN22PT | Missense | g.chr7:106296714G > A | c.1472G > A | p.G491E |
| | | HNPTS_42 | Missense | g.chr7:106508473C > T | c.467C > T | p.A156V |
| PTEN | NM_000314 | HN_00190 | Missense | g.chr10:89692792C > G | c.1307C > G | p.D92E |
| | | HN_62652 | Splice_Site_SNP | g.chr10:89712017G > A | c.e7_splice_site | |
| | | HN_62741 | Missense | g.chr10:89717729G > T | c.1785G > T | p.D252Y |
| | | HN_62863 | Missense | g.chr10:89717712C > T | c.1788C > T | p.P246L |
| | | HN_63039 | Nonsense | g.chr10:89720852C > T | c.2034C > T | p.R335* |
| | | HNPTS_1 | Missense | g.chr10:89624268G > T | c.42G > T | p.R14S |
| PIK3R5 | NM_014308 | HNPTS_16 | Missense | g.chr17:8792082G > A | c.1022C > T | p.A341V |
| | | HNPTS_22 | Missense | g.chr17:8808132T > C | c.374A > G | p.E125G |
| | | HNPTS_29 | Missense | g.chr17:8792140C > T | c.964G > A | p.C322K |
| | | HNPTS_38 | Nonsense | g.chr17:8812417C > T | c.178G > T | p.E60* |
| PIK3AP1 | NM_152309 | HN_62506 | Missense | g.chr10:98469347C > T | c.535C > A | p.A136D |
| | | 91 | Missense | g.chr10:98781183C > T | c.1433G > A | p.R478Q |
| | | 266 | Missense | g.chr10:98398536G > C | c.1055C > G | p.T352S |
| | | HN22PT | Missense | g.chr10:98401046C > G | c.937G > C | p.G313R |
| PIK3R1 | NM_181523 | HN_00361 | In_frame_Ins | g.chr5: 67589591_67589592insATA | c.1914_1915insATA | p.453_454insN |
| | | HN_62338 | Missense | g.chr5:67576786A > G | c.1428A > G | p.I290V |
| | | HN_62421 | Missense | g.chr5:67591085G > C | c.2238G > C | p.D560N |
| | | HNPTS_6 | Nonsense | G.chr5: 67591278_67591279GA > CT | c.1776_1777GA > CT | p.592_593KK > N* |
| PIK3C2G | NM_004570 | HN_00190 | Missense | g.chr12:18534785G > T | c.2044G > T | p.V656L |
| | | HNPTS_23 | Frame_Shift_Ins | g.chr12: 18435201_18435202insT | c.186_187insT | p.T62fs |
| | | HNPTS_29 | Missense | g.chr12:18719918C > T | c.3815C > T | p.S1272L |
| MTOR | NM_004958 | HN_62421 | Missense | g.chr1:11182067A > T | c.6900T > A | p.L2260H |
| | | HN_62469 | Missense | g.chr1:11272448C > T | c.3600G > A | p.R1161Q |
| PIK3C2A | NM_002645 | HN_62699 | Splice_Site_SNP | g.chr11:17167490C > T | c.e6_splice_site | |
| PIK3C2B | NM_002646 | HN_62739 | Missense | g.chr1:204426879G > A | c.2169C > T | p.R564C |
| PIK3CD | NM_005026 | HN_62672 | Missense | g.chr1:9780202A > T | c.1475A > T | p.T423S |
| PIK3R6 | NM_001010855 | HN_62860 | Missense | g.chr17:8730556C > T | c.1688G > A | p.R483H |
| PIK3IP1 | NM_052880 | HNPTS_1 | Missense | g.chr1:231685563C > A | c.430G > T | p.A144S |
| AKT2 | NM_001626 | HNPTS_45 | Missense | g.chr19:40741920T > C | c.1052A > G | p.Y351C |
| TSC1 | NM_000368 | HN_00761 | Nonsense | g.chr9:135796754G > A | c.967C > T | p.R245* |
| TSC2 | NM_000548 | HNPTS_42 | Nonsense | g.chr16:2134999C > G | c.4541C > G | p.S1514* |
| RICTOR | NM_152756 | HNPTS_18 | Nonsense | g.chr5:38944564C > A | c.4897G > T | p.E1633* |
| | | HNPTS_27 | Missense | g.chr5:38991111C > G | c.523G > C | p.D175H |
| RPTOR | NM_020761 | HNPTS_17 | Missense | g.chr17:78820280C > T | c.1220C > T | p.P407L |
| MAPK Pathway Component | | | | | | |
| HRAS | NM_005343 | HN_00466 | Missense | g.chr11:533875G > T | c.369C > A | p.Q61K |
| | NM_005343 | HN_62469 | Missense | g.chr11:534285C > A | c.226G > T | p.G13V |
| | NM_005343 | HN_62863 | Missense | g.chr11:534288C > G | c.223G > C | p.G12A |
| | NM_005343 | HN_63080 | Missense | g.chr11:534288C > T | c.223G > A | p.G12D |
| | NM_001130442 | HN11PT | Missense | g.chr11:523874T > A | c.182A > T | p.Q61L |
| | | HN12PT | Missense | g.chr11:524286C > G | c.37G > C | p.G13R |
| | | 166 | Missense | g.chr11:524288C > T | c.35G > A | p.G12D |
| KRAS | NM_033360 | HN_62421 | Missense | g.chr12:25378557C > G | c.622G > C | p.K147N |
| | NM_033360 | HNPTS_23 | Missense | g.chr12:25368473T > C | c.472A > G | p.T158A |
| RAF1 | NM_002880 | 478 | Missense | g.chr3:12601123G > C | c.1837G > C | p.L613V |
| SHC2 | NM_012435 | HNPTS_26 | Missense | g.chr19:436383T > C | c.823A > G | p.R275G |
| SHC3 | NM_016848 | HNPTS_4 | Missense | g.chr9:91656972G > A | c.1329G > T | p.E443D |
| JAK/STAT Pathway Component | | | | | | |
| JAK1 | NM_002227 | HNPTS_14 | Missense | g.chr1:65335021T > A | c.620A > T | p.Q207L |
| | | HNPTS_18 | Missense | g.chr1:65307005C > G | c.2572G > C | p.E858Q |
| JAK2 | NM_004972 | HNPTS_17 | Missense | g.chr9:5054676C > A | c.728G > A | p.C243Y |
| JAK3 | NM_000215 | HNPTS_20 | Missense | g.chr19:17949121T > A | c.1520A > T | p.Q507L |
| | | HN_62376 | Nonsense | g.chr19:17955190G > A | c.137C > T | p.Q13* |
| | | HN_63080 | Missense | g.chr19:17942173G > A | c.2342G > T | p.R948C |
| | | HN33PT | Missense | g.chr19:17812143A > T | c.1150T > A | p.F384I |
| STAT1 | NM_007315 | HN_63080 | Missense | g.chr2:191856003G > T | c.1376C > A | p.Q330K |
| | NM_139266 | 388 | Missense | g.chr2:191548805C > T | c.2113G > A | p.E705K |
| STAT3 | NM_139276 | HN_01000 | Missense | g.chr17:40498671C > G | c.429G > C | p.E63D |
| STAT5B | NM_012448 | HN_62338 | Missense | g.chr17:40375520T > A | c.599A > T | p.I144F |
| IL6ST | NM_002184 | HN_62415 | Missense | g.chr5:55247378T > A | c.2009A > T | p.D585V |
| | | HN_62469 | Missense | g.chr5:55250817G > A | c.1526C > T | p.T424I |
| | | HNPTS_21 | Missense | g.chr5:55250717C > A | c.1371G > T | p.W457C |
| IL6R | NM_000565 | HNPTS_1 | Missense | g.chr1:154427027G > C | c.1130G > C | p.G377A |

6. EXAMPLE 1: MUTATIONS IN PIK3CA, PTPRT AND PTPRD ARE DRIVER MUTATIONS

6.1 Results

Figure 2B:
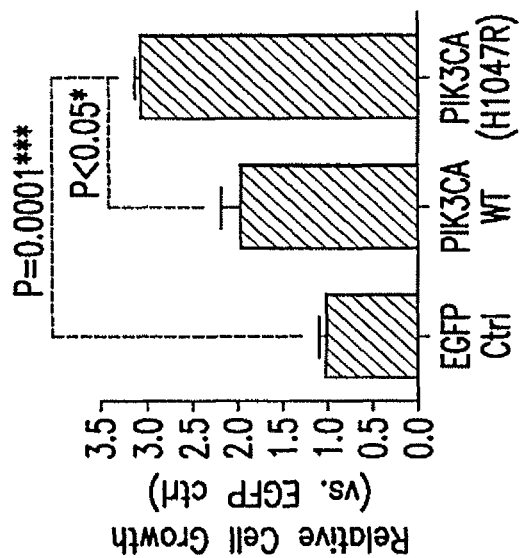
Figure 2A:
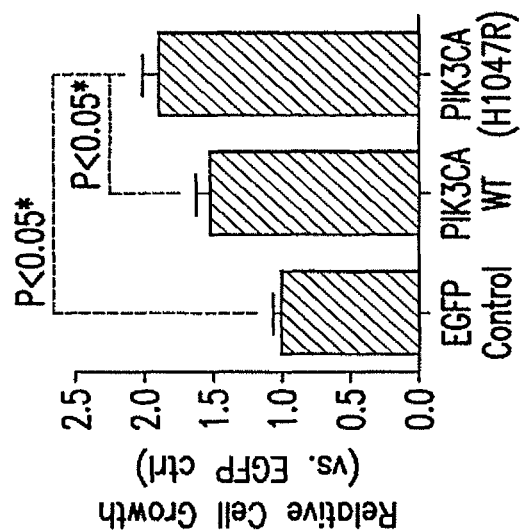
Figures 2C, 2D:
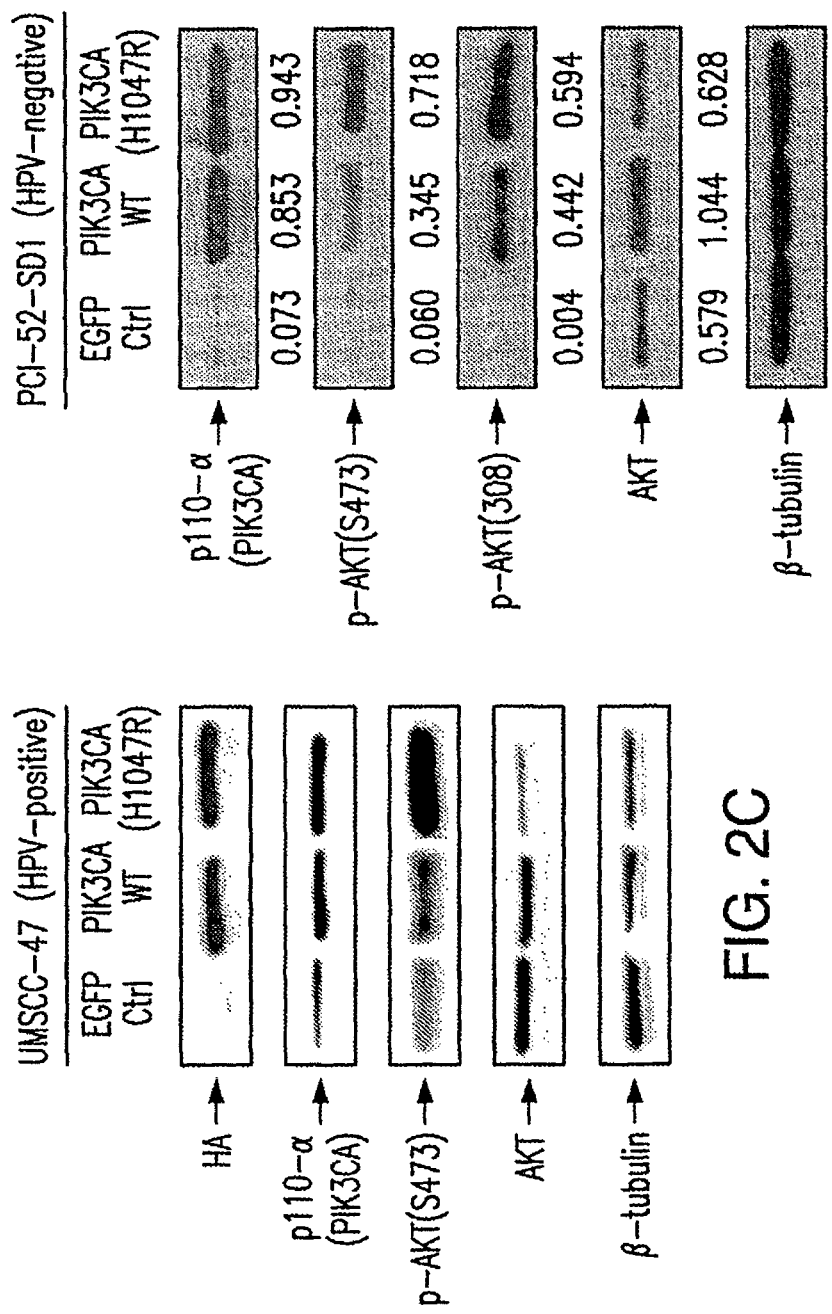

Mutations of the PIK3CA are known oncogenic "driver" mutations in other solid tumors. We detected PIK3CA mutations in nearly 30% of HPV-HNSCC and in a smaller subset of HPV-negative HNSCC tumors. In addition, amplification of the PIK3CA gene was found in 18% of HPV-HNSCC, which also represents a potential mechanism to drive tumor progression. To determine the effect of PIK3CA overexpression or mutation on survival, HPV+SD (UM-SCC47) and HPV(−)SD (PCI-52) cells were infected with retroviruses expressing the control EGFP gene, or PIK3CA wildtype (WT), or a representative mutant PIK3CA (H1047R), and then subjected to serum withdrawal (0% FBS) for 1 week. The protein expression levels of the transfected genes (detected by antibody against p110-α for PIK3CA) were comparable in both mutant and WT-transfected cells (FIG. 2A-D). Cells expressing the mutant PIK3CA protein exhibited a significant increase in cell survival (and/or proliferation) under serum withdrawal conditions relative to cells expressing PIK3CA WT or EGFP control (FIGS. 2A and 2B). Activation of PI3K signaling can be assessed biochemically by determining levels of phosphorylated downstream components including AKT, PDK1 and p70S6K, among other proteins. Increased activation of the PI3K pathway, as indicated by elevated levels of phosphorylated AKT, was detected in both PIK3CA mutant and WT-expressing cells derived from HPV-positive and HPV-negative HNSCC cells (FIGS. 2C and 2D). Neither UMSCC-47 nor PCI-52 harbor PIK3CA mutations, making them ideal models for the introduction of WT or mutated genes.

In addition to known driver mutations, we have also found that previously unappreciated alterations can drive tumor progression through loss of function of a tumor suppressor leading to activation of an oncogenic protein. For example, mutations of protein tyrosine phosphatase receptor types T and D (PTPRT and PTPRD) have been reported in carcinomas of the lung (18%), colon (26%), head and neck, as well as gliomas. In our mutation cohort, we found 4 tumors with PTPRD mutations, 3 tumors with PTPRT mutations and 17 tumors with mutations of other members of the PTPR family for an incidence of 31.1% (23/74; with one tumor carrying both PTPRD and PTPRT mutations) (FIG. 3).

Preliminary analysis of the HNSCC TCGA cohort demonstrates mutations in PTPR family members in 39% of cases (240 tumors with completed whole exome sequencing to date). Mutations in the protein tyrosine phosphatase catalytic domains (PTPRT and PTPRD) and the fibronectin type 3 domain (PTPRD) have been reported to inhibit cellular functions or the phosphatase activity of these proteins. It is noteworthy that activating mutations of the upstream activators of STAT3 in HNSCC including EGFR, JAK, and Src were not detected in our HNSCC cohort.

We hypothesized that loss of function of PTPRT or PTPRD would be expected to increase STAT3 activation and hence serve as "driver" mutations. To test this hypothesis and determine the effects of PTPRT or PTPRD mutations on STAT3 activation in HNSCC, a representative PTPRT mutation and a representative PTPRD mutation identified in human HNSCC tumors were cloned and introduced into HNSCC cells followed by determination of pSTAT3 levels. Expression of mutated PTPRT in HNSCC cells significantly increases STAT3 activation (FIG. 4A), survival in low serum conditions (FIG. 4B) and invasion. Similar findings were observed with the PTPRD mutation (PI31IT) (FIG. 10).

6.2 Discussion

The above results provide support for use of the above oncogene screening model in assessing the functional consequences of both direct and indirect driver mutations in cancer.

In addition to oncogene screening, this model can also be used in drug discovery. Specifically, cells expressing mutations that confer increased survival can then be screened against panels of therapeutic agents to determine if the mutation(s) can predict the optimal treatment for patients whose tumors harbor the mutation(s). For example, PI3K pathway inhibitors have been reported to demonstrate enhanced efficacy in patients with breast and gynecologic malignancies whose tumors harbor PIK3CA mutations. We tested whether activation of PI3K signaling through gain-of-function mutations in PIK3CA would increase PI3K activation and serve as biomarkers for treatment with a PI3K inhibitor in HNSCC models. To determine the effects of individual PIK3CA mutations on sensitivity to PI3K pathway inhibitors in HNSCC, we tested the effects of a representative PI3K pathway inhibitor (BEZ-235) in HPV-HNSCC cells engineered to express mutant or WT PIK3CA (E542K) a HNSCC line harboring a PIK3CA mutation. These cells were more sensitive to BEZ-235 treatment than vector control transfected cells (FIG. 5).

Similarly, cells engineered to express a representative PTPRT mutant that led to STAT3 activation were more sensitive to the growth inhibitory effects of a preclinical STAT3 inhibitor (FIG. 6). Overall, our models can be used to determine if the mutation detected in a human tumor is important for tumor growth and facilitate selection of the appropriate therapeutic agents.

7. EXAMPLE 2: RECEPTOR PROTEIN TYROSINE PHOSPHATASE MUTATIONS IN HEAD AND NECK CANCER

7.1 Materials and Methods

Mutation Databases.

HNSCC mutation analyses were based on the published whole exome sequencing data on 74 HNSCC tumors [10] and the TCGA. PTPR and PTPN mutation rates (% mutated tumors) were calculated by the actual % of tumors harboring non-synonymous mutations of PTPR or PTPN members. For multi-cancer analysis, mutation data (from whole-exome sequencing) were obtained from the cBio portal [11].

Cell Cultures.

All HNSCC cell lines were genotypically verified and maintained in complete DMEM medium containing 10% fetal calf serum, IX penicillin/streptomycin solution (Invitrogen, Carlsbad, USA) in a humidified cell incubator at 37° C., 5% CO2. 686LN cells were obtained from Dr. Georgia Chen and the PCI-52-SD1 cell line was obtained by clonal selection of the parental PCI-52 cell line (University of Pittsburgh Cancer Institute) by rounds of graded serum-selection. In brief, PCI-52 parental cell lines were plated as single cell, which grew as single clones. These single clones were subjected to serum-deprived conditions (5%, 2%, 1% and 0% FBS vs 10% FBS condition) for 1-2 weeks, followed by assessment of cell growth by MTT assay. The PCI-52-SD1 subline was the most serum-sensitive subline, which die (>99.8%) upon complete serum deprivation.

Plasmid Constructs and Site-Directed Mutagenesis.

pMXs-puro-EGFP vector was obtained from Cell Biolabs, San Diego, Calif. PTPRT WT gene was subcloned into the retroviral viral vector and the pMXs-puro-PTPRT WT was used as a template for site directed mutagenesis using the QuikChange Site-Directed Mutagenesis Kit according to the manufacturer's instructions (Stratagene, La Jolla, Calif.). All mutation sites as well as the full-length cDNA were sequenced confirmed.

Retroviral Infection of HNSCC Cells.

Retroviruses were generated using the Platinum Retrovirus Expression Systems (Cell Biolabs, San Diego, Calif.) according to manufacturer's instructions. Briefly, Plat A cells were transfected with 3 μg of retroviral vector carrying the gene of interest (pMXs-puro-EGFP as control, pMXs-puro-PTPRT WT, pMXs-puro-PTPRT mutants). Three days after transfection, fresh retroviruses (in the supernatant of the Plat-A cells) were collected by centrifugation at 1,500 rpm for 5 mins at 4° C. Cell debris was removed by filtering through a 0.45 μm syringe filter. Fresh retroviruses were used for infection of HNSCC cells. HNSCC cells were plated at 20% confluency in a T75 flask one day before infection. Infection of HNSCC cells was performed by adding 4.5 ml of retrovirus to the cells containing 7.5 ml of complete culture media. Then, 38 μl of polybrene (4 μg/μl, Sigma-Aldrich, St. Louis, Mo.) was added to the cells with gentle mixing. Cells were then incubated at 37° C. and 5% CO2 for additional 48-72 hrs, and the infection medium was replaced with fresh complete medium after infection. Expression of the gene of interest and the alteration of signaling pathway was then performed within 7-10 days of infection.

Immunoblotting.

Western blotting was performed as previously described [12]. Primary antibodies for p-STAT3(Tyr705) and STAT3 were purchased from Cell Signaling Technology, Inc. (Boston, Mass.). Anti-tubulin antibody was from Abcam (Cambridge, Mass.) and secondary antibodies from BioRad (Hercules, Calif.).

Molecular Modeling.

Crystal structure of human PTPRT catalytic domain 1 (PDB: 2OOQ) [5] and crystal structure of catalytic domains 1 and 2 of human protein phosphatase gamma (PDB: 2NLK) [5] were used as templates for homology modeling of human PTPRT (amino acids 862-1441, covering the PTPase domains 1 and 2) using the program Modeller version 9v8 [6]. A substrate, p-Tyr, was modeled into the catalytic sites of both domains 1 and 2 of PTPRT upon superposition with a structurally highly similar crystal structure of the human tyrosine phosphatase PTPN5 (C472S catalytic inactive mutant) in complex with p-Tyr (PDB: 2CJZ) (the root-mean-square deviation between 2OOQ and 2CJZ is 1.85 Å). Surface residues of the PTPRT PTPase domain 1 and 2 were divided into three groups according their distance from the bound p-Tyr (within 0-5 Å, 5-12 Å and 12-25 Å).

7.2 Results

To determine the status of the entire PTPR family, analysis of a whole exome mutational profile of 347 primary head and neck squamous cell carcinomas (HNSCCs) was performed. Strikingly, 30.0% (104/347) of HNSCC tumors harbored non-synonymous somatic mutations of at least one PTPR family member, as compared to only 14.1% (49/347) of tumors with mutations of PTPNs (FIG. 7A). Further, 7.4% (25/347) of HNSCC tumors contained multiple mutations of PTPR family members (from 2-6 PTPR mutations/tumor; FIG. 7B; see TABLE 2 for all PTPR mutations in HNSCC). Further investigation demonstrated that this high rate of somatic mutation of the PTPR family (vs. PTPN family) is found in all 15 types of human solid tumors sequenced to date by The Cancer Genome Atlas (TCGA) (4115 solid tumors), but not in the sequenced blood malignancy (199 cases of AML) (FIG. 7C and TABLE 3).

Among the 347 sequenced HNSCC tumors, PTPRT is the most frequently mutated PTPR (5.5% cases; 20 mutations total, with one tumor harboring 2 PTPRT mutations), followed by PTPRC and PTPRD (TABLE 2). Although PTPR mutation rates vary among different cancer types, cumulative data reveal that PTPRT is the single most commonly mutated PTPR in human cancers (5.3%, 276 mutations in 229/4314 cases sequenced by TCGA) (TABLE 3). In contrast to HNSCC, thyroid cancers harbor a substantially lower rate of PTPR mutation and an extremely low rate of PTPRT mutation (1/324 cases; 0.3%), distinguishing the genomic aberration profiles of these 2 cancers of the head and neck region. PTPR mutations in HNSCC were not found to be associated with HPV status (P=0.86; PTPR mutations in 13/42 HPV-positive tumors vs 91/305 HPV-negative tumors), or mutations of TP53 (P=0.45), NOTCH1 (P=0.54), PIK3CA (P=0.29) or HRAS (P=0.40).

Figure 7D:
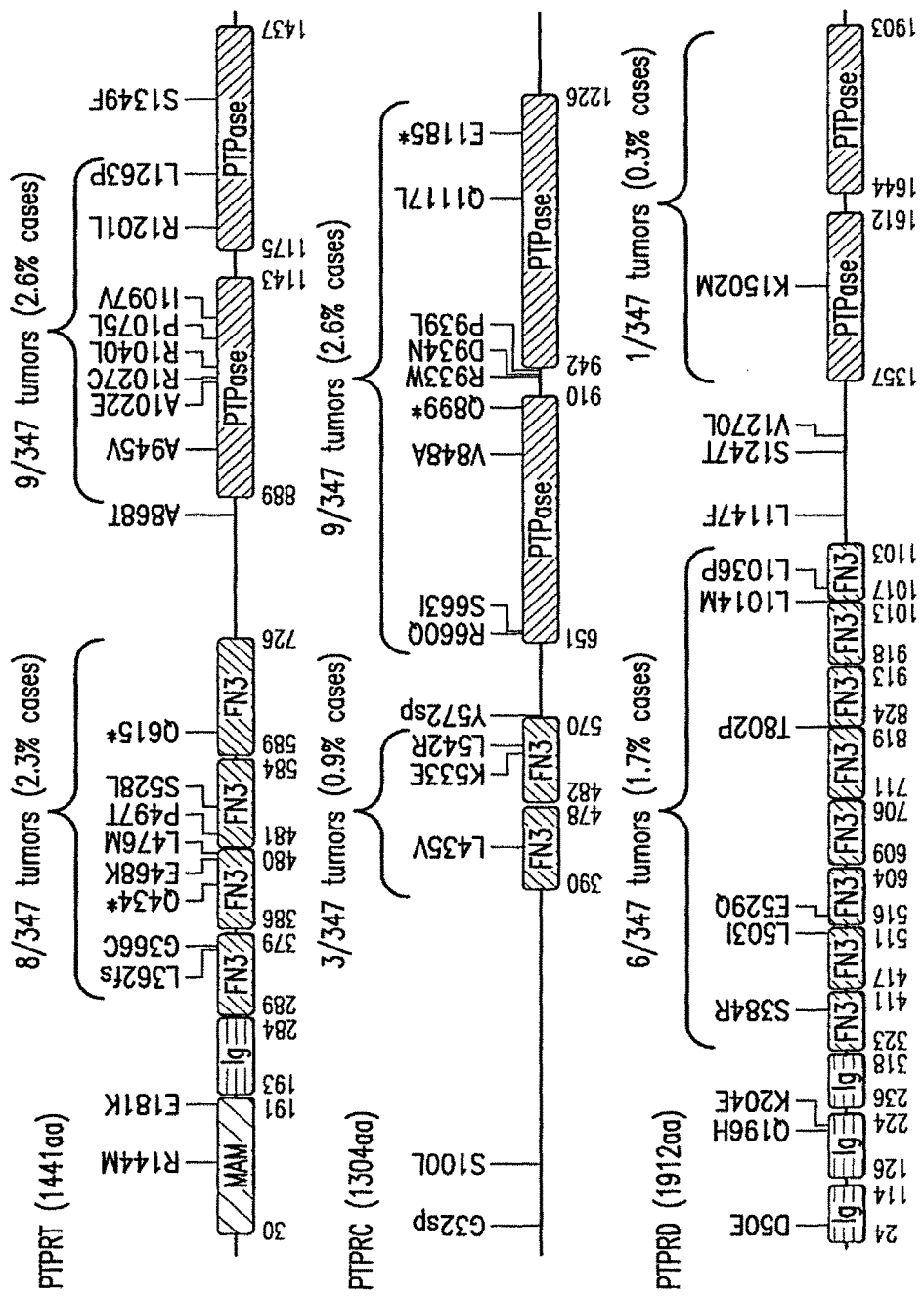

The PTPRs are a family of integral membrane protein tyrosine phosphatases. Major domains found in all PTPRs include the extracellular fibronectin type Ill-like (FN3) repeats and the intracellular catalytic phosphatase (PTPase) domains. Cumulative mutation data for PTPRT in all cancers sequenced to date indicates that 37.0% (102/276) of PTPRT mutations are found in the PTPase domain, while 33.7% (93/102) occur in the FN3 domain. In HNSCC, 45.0% (9/20) of PTPRT mutations are located in the PTPase domain (FIG. 7D). The mutation sites of the most frequently mutated PTPR members (PTPRT/C/D) in HNSCC are shown in FIG. 7D (all other PTPR mutations are shown in FIG. 9).

The biologic/functional consequences of the tumor-derived PTPR mutations in HNSCC are largely unknown. To determine whether HNSCC PTPRT mutations act as "drivers", a serum-dependent HNSCC cell line (PCI-52-SD1) that undergoes rapid cell death upon serum withdrawal was developed. Using this model, stable expression of two representative mutants (calculated to result in both charge and amino acid size changes; TABLE 4), PTPRT(R1040L) and PTPRT(A1022E) conferred increased survival following serum deprivation, relative to that seen following expression of wild-type PTPRT (FIG. 8A), confirming a "driver" phenotype for the mutant.

Given that a high percentage of PTPRT mutations are located within the enzymatic (PTPase) domain, the potential impact of the mutations on interactions between the catalytic domains and phospho-tyrosine substrate was determined using a molecular modeling approach. Although the structure of a PTPRT-p-Tyr protein complex is not available, the X-ray crystallographic structure of the PTPRT phosphatase domain alone has recently been resolved (PDB: 2OOQ) [5]. Therefore, by homology modeling [6], the approximate substrate-interacting surface of the PTPRT PTPase domains 1 and 2 (FIGS. 8B-D) based on the highly similar (to PTPRT) crystal structure of human tyrosine phosphatase PTPN5 in complex with p-Tyr was determined. Using this model, we localized several cancer-related PTPRT mutations to the substrate-interaction surface of the PTPRT PTPase domains 1 and 2 in close proximity to incorporated p-Tyr (D905, R928, H1053, G1089 and V1124 in domain 1; Q1180, R1201, R1207, P1213, Q1286, T1346, N1380, G1382 and R1384 in domain 2). Mutations previously shown to decrease the PTPRT phosphatase activity were also found in proximity to p-Tyr regions (C1084, D1052, Y893, Q965, R1188 and T1346) [7,8]. Of note, additional cancer-associated nonsense (*) mutations and frameshift (fs) mutations are likely to alter the PTPRT structure and impact substrate interactions (L362fs, Q434* and Q615* found in HNSCC, and E1227*, R1207*, E1155*, R1358*, and G1386* in other cancers; COSMIC database). These results suggest that PTPRT PTPase domain mutations, which are found in human cancers, likely interfere with enzymatic activity and/or substrate interaction.

Figure 8A:
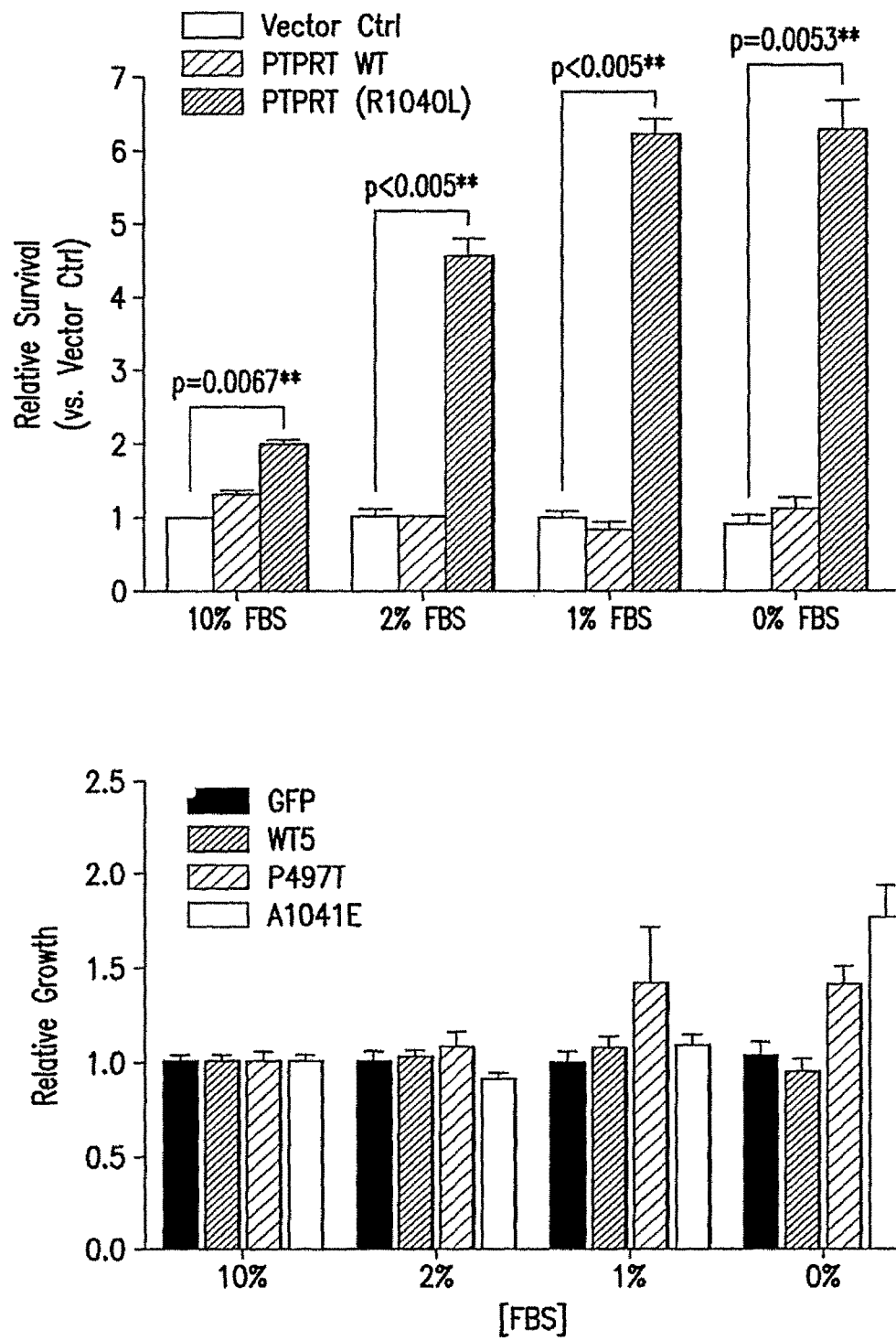
Figures 8B, 8C:
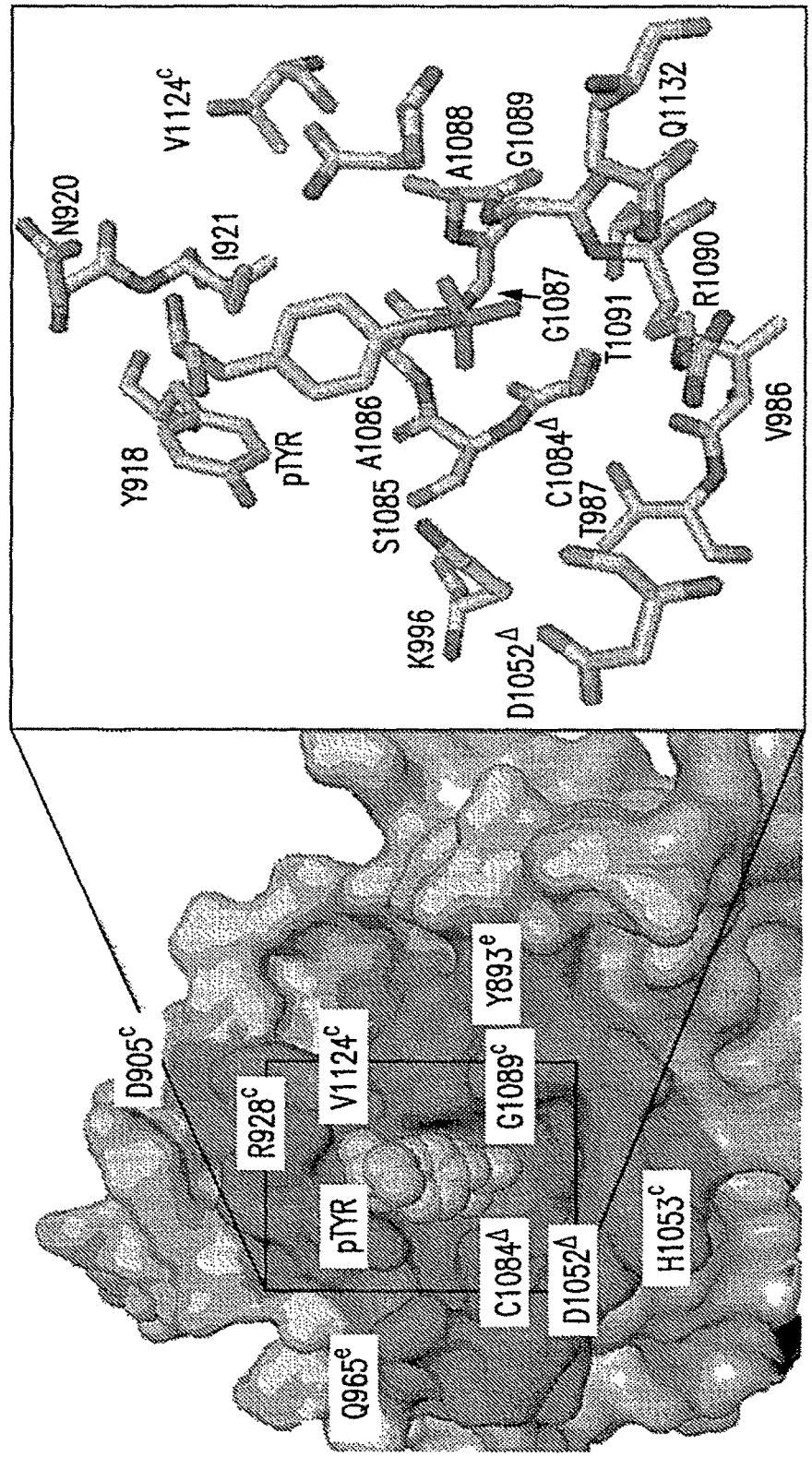
Figures 8D, 8E:
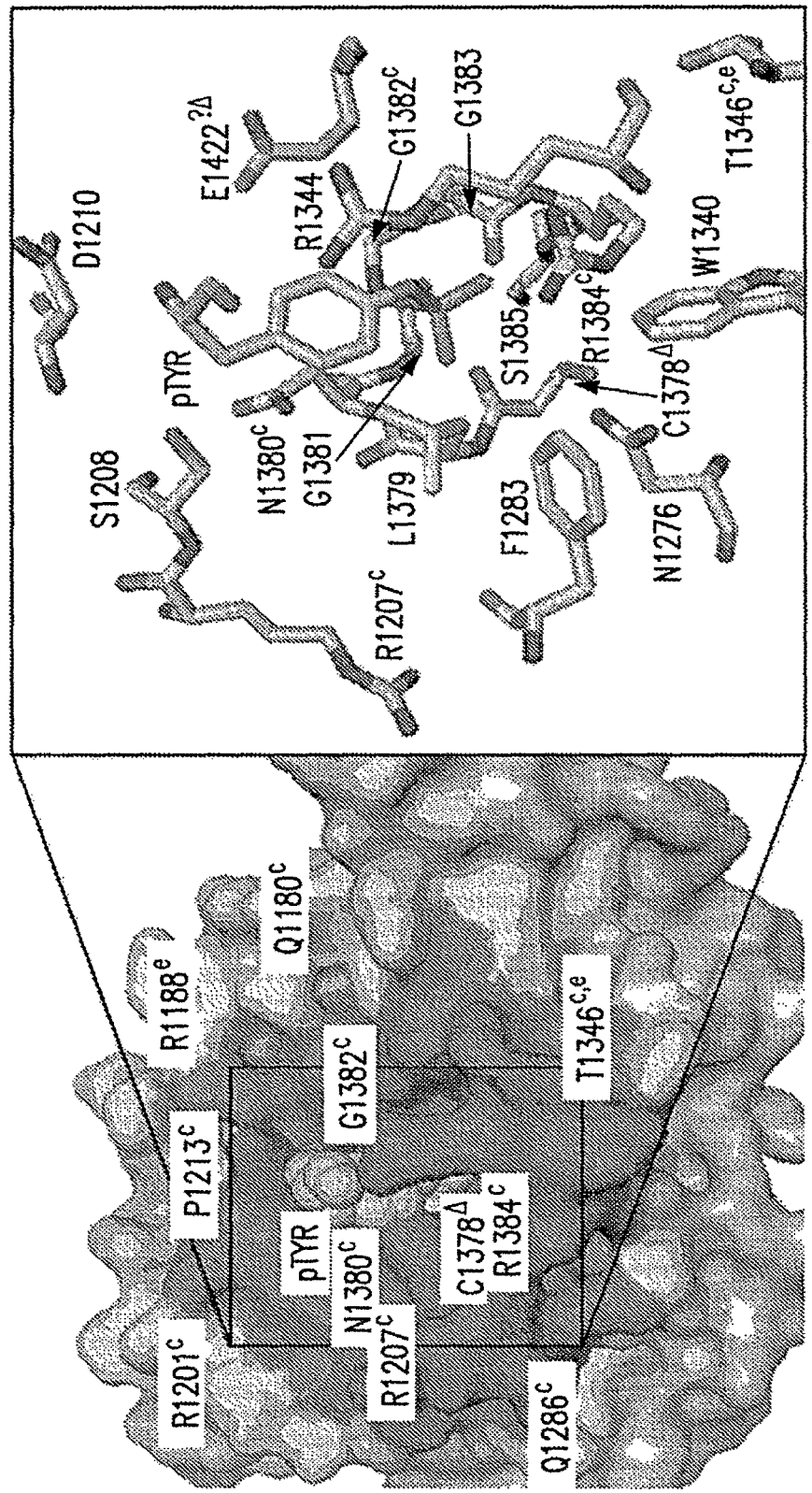
Figure 8F:
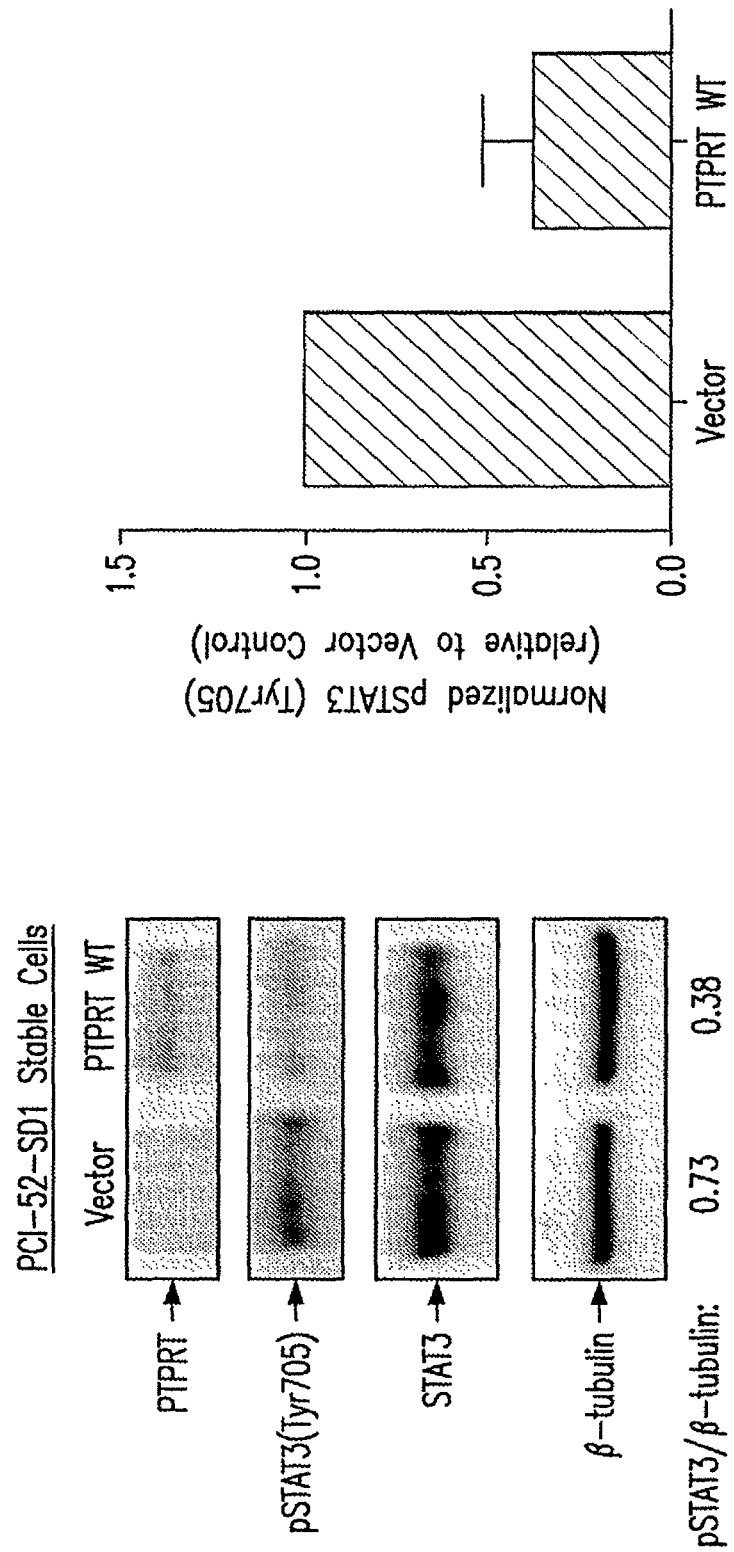
Figure 8G:
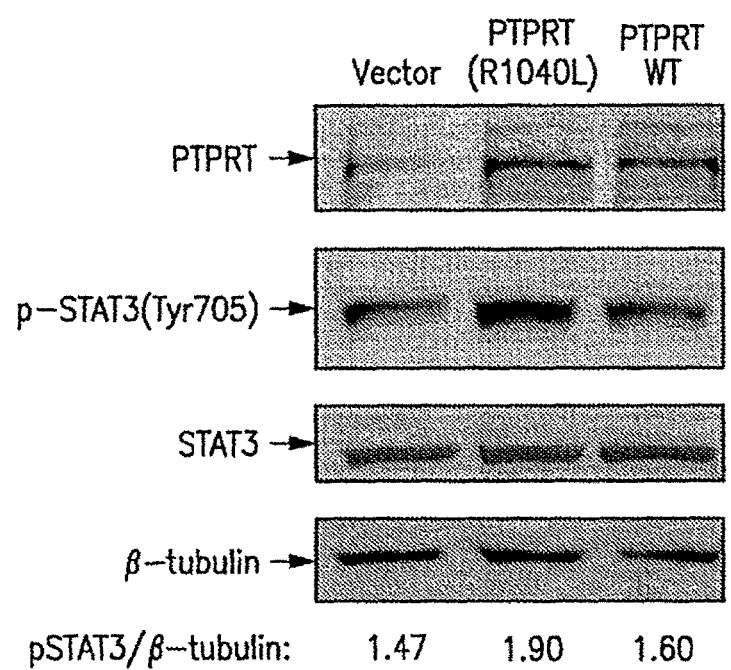
Figure 9A:
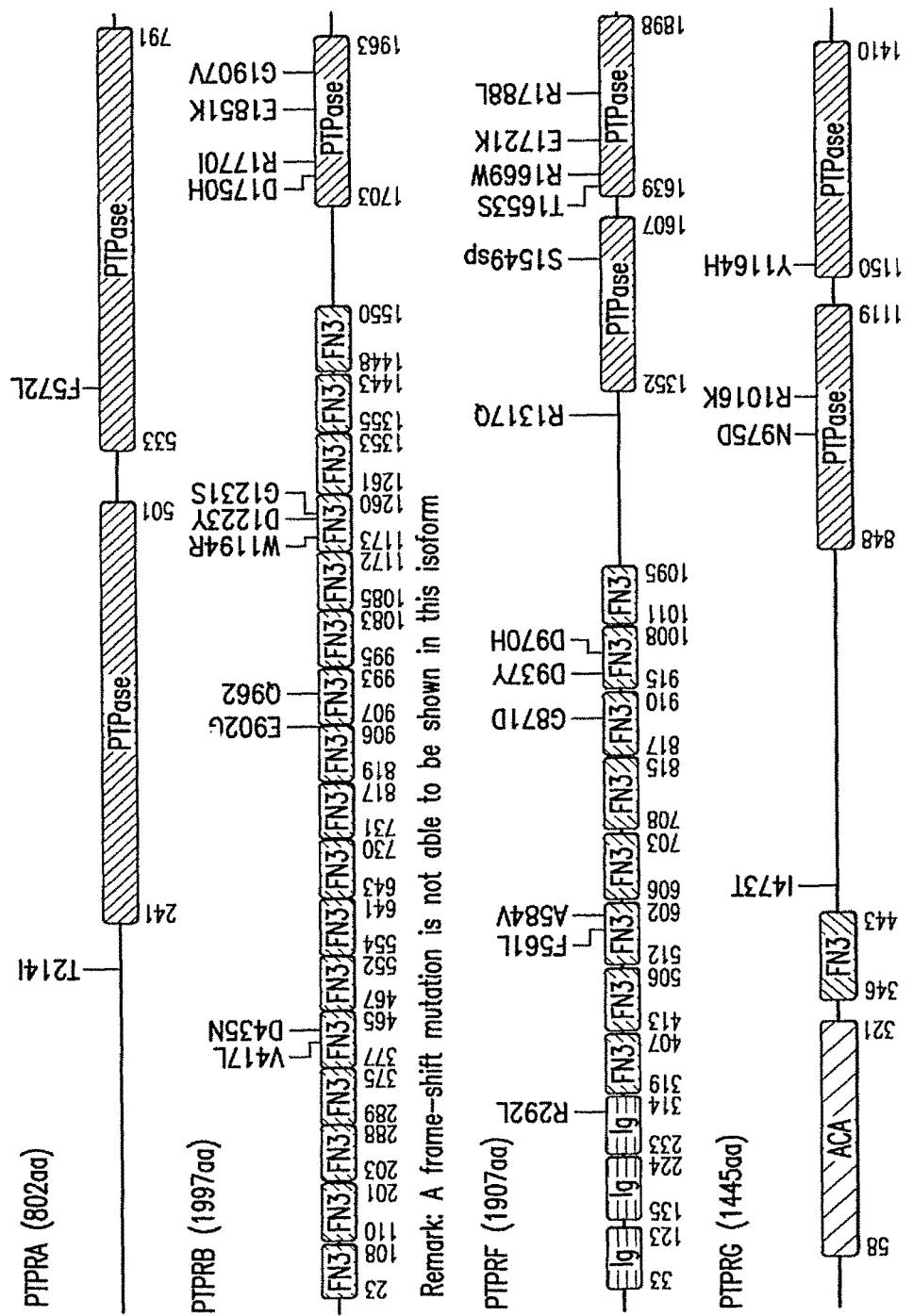
Figure 9B:
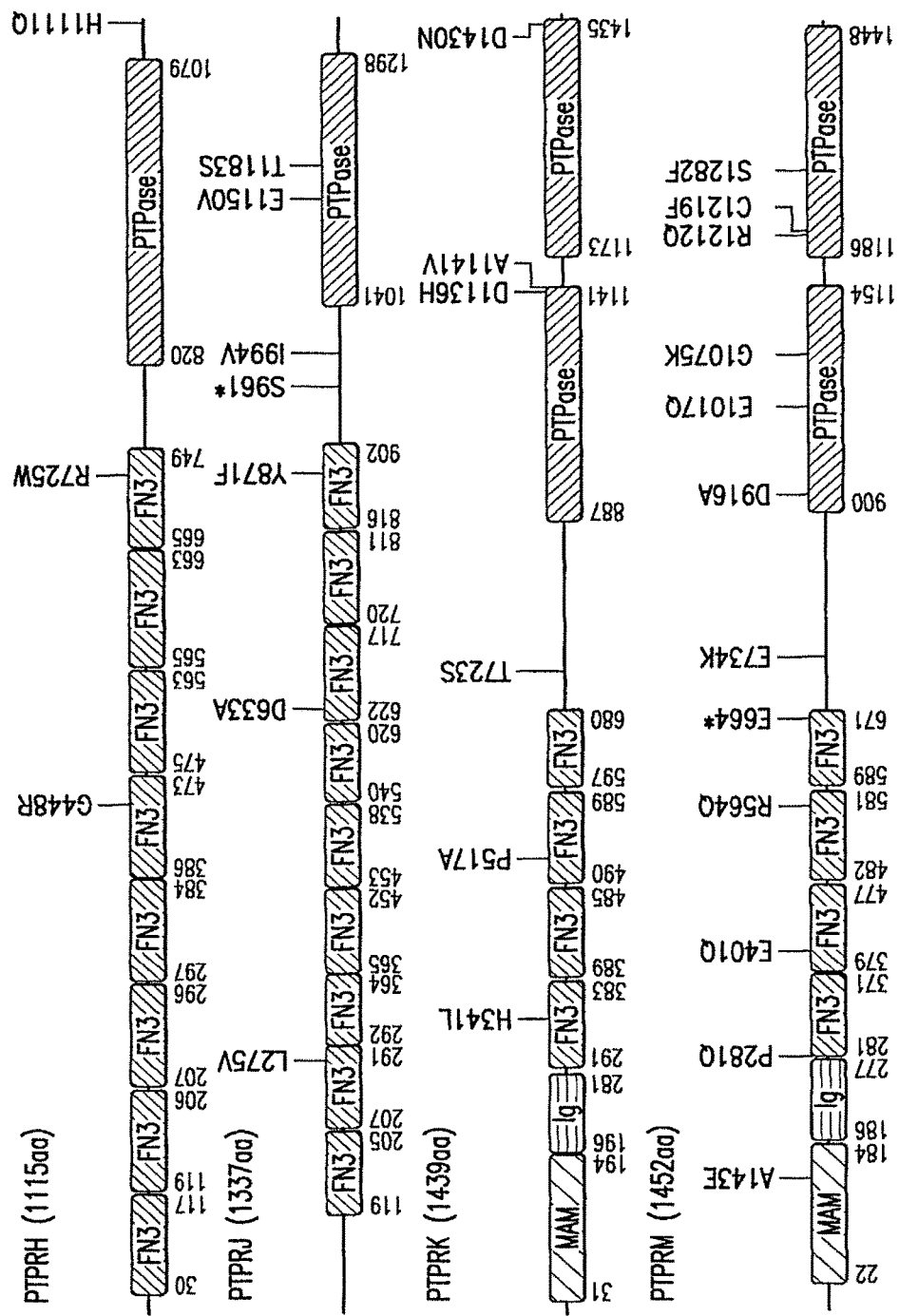
Figure 9C:
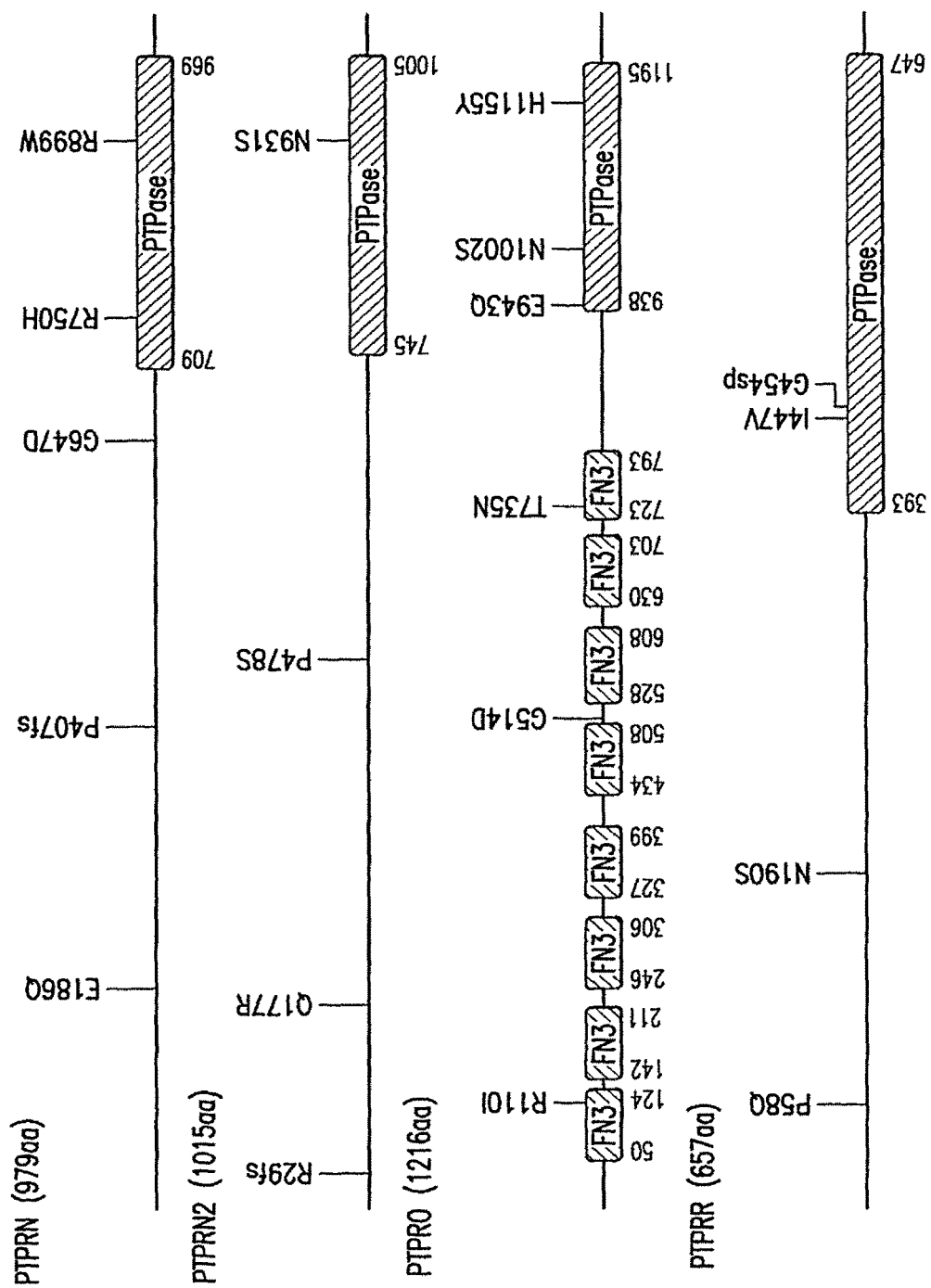
Figure 9D:
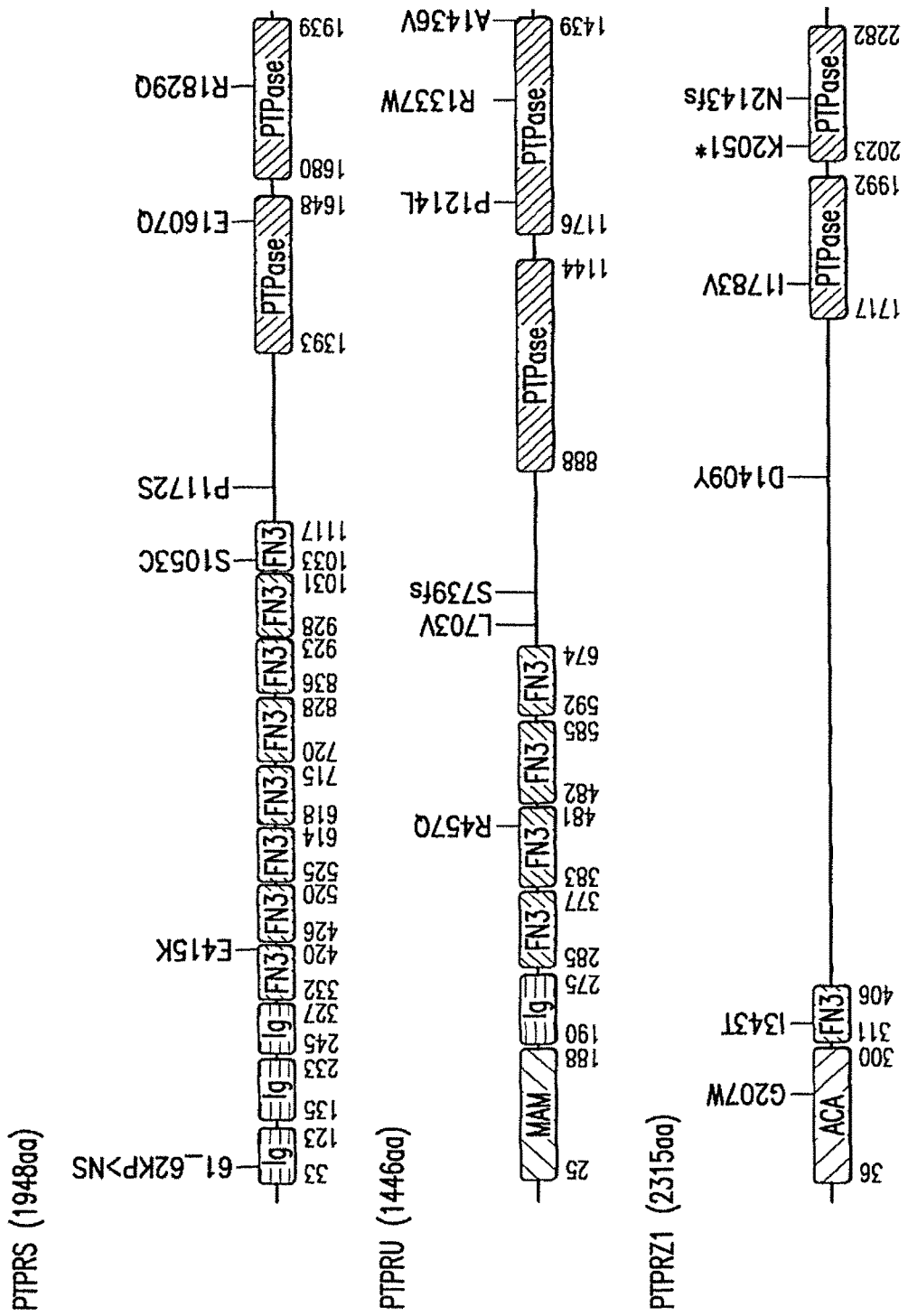

Based on these findings, it was hypothesized that the PTPRT mutations identified in HNSCC may impair the phosphatase activity of the enzyme, resulting in increased phosphorylation of PTPRT substrates, including the oncogenic transcription factor STAT3. STAT3 is hyperactivated in the majority of HNSCCs and has been reported to serve as a direct substrate of PTPRT4. Stable expression of wild-type PTPRT in PCI-52-SD1 cells resulted in reduction of basal pSTAT3 levels by ~60% (FIG. 8F), confirming regulation of STAT3 by PTPRT in HNSCC cells. Expression of the PTPRT(R1040L) phosphatase domain mutant in PCI-52-SD1 cells resulted in increased pSTAT3 levels, relative to vector-transfected control cells (FIG. 8G). Expression of additional PTPRT mutants with mutations in the PTPase domain, A1022E and A1041E, in HNSCC cells also resulted in significant upregulation of pSTAT3 (FIG. 10).

7.3 Discussion

The above results show that mutations in PTPRT act as driver mutations. Additionally, these data support the contention that HNSCC-associated PTPRT mutations can alter STAT3 phosphorylation/activation. Moreover, our findings suggest a novel, and potentially common mechanism for dysregulated cell survival and growth in HNSCC, involving PTPRT mutation and STAT3 hyperactivation. In view of the high frequency of PTPR mutations in other cancers, this mechanism may be broadly relevant in a number of different malignancies.

TABLE 2

| Annotated Gene | Reference GenBan Seq. | No. of Synonymous Mutations | No. of Non-synonymous Mutations | No. of Tumors with Mutations | Mutation Frequency | Mutation Type | Genomic Change | Allele Change | Amino Acid Change |
|---|---|---|---|---|---|---|---|---|---|
| PTPRA | NM_002836 | 0 | 2 | 2 | 0.58% | Missense | g.chr20:3007774 | C > G | p.F583L |
| | | | | | | Missense | g.chr20:2969023 | C > T | p.T225I |
| PTPRB | NM_002837 | 4 | 12 | 12 | 3.46% | Missense | g.chr12:70954562 | C > A | p.D1223Y[†] |
| | | | | | | Missense | g.chr12:70928431 | C > T | p.E1851K |
| | | | | | | Missense | g.chr12:70929923 | C > A | p.R1770I |
| | | | | | | Nonsense | g.chr12:70963581 | G > A | p.Q952* |
| | | | | | | Missense | g.chr12:70931979 | C > G | p.D1750H |
| | | | | | | Missense | g.chr12:70954649 | A > T | p.W1194R |
| | | | | | | Missense | g.chr12:70925945 | C > A | p.G1907V |
| | | | | | | Missense | g.chr12:70983837 | C > T | p.D435N |
| | | | | | | Missense | g.chr12:70954538 | C > T | p.G1231S |
| | | | | | | Missense | g.chr12:70983891 | C > A | p.V417L |
| | | | | | | Missense | g.chr12:70964817 | T > C | p.E902G |
| | | | | | | Frame_Shift_Del | g.chr12:71029580 | delA | p.S108fs |
| PTPRC | NM_002838 | 7 | 15 | 14 | 4.03% | Splice_Site_SNP | g.chr1:198697468 | G > C | Unknown |
| | | | | | | Missense | g.chr1:198701439 | G > A | p.R660Q |
| | | | | | | Missense | g.chr1:198687375 | A > G | p.K533E |
| | | | | | | Missense | g.chr1:198701448 | G > T | p.S663I |
| | | | | | | Missense | g.chr1:198713307 | C > T | p.P939L |
| | | | | | | Missense | g.chr1:198668699 | C > T | p.S100L |
| | | | | | | Missense | g.chr1:198711143 | T > C | p.V848A |
| | | | | | | Nonsense | g.chr1:198723447 | G > T | p.E1185* |
| | | | | | | Missense | g.chr1:198685828 | C > G | p.L435V |
| | | | | | | Missense | g.chr1:198721748 | A > T | p.Q1117L |
| | | | | | | Missense | g.chr1:198687403 | T > G | p.L542R |
| | | | | | | Missense | g.chr1:198713288 | A > T | p.R933W |
| | | | | | | Missense | g.chr1:198713291 | G > A | p.D934N |
| | | | | | | Splice_Site | g.chr1:198665840 | G > A | p.G32_splice |
| | | | | | | Nonsense | g.chr1:198713186 | C > T | p.Q899* |
| PTPRD | NM_002839 | 2 | 13 | 13 | 3.75% | Missense | g.chr9:8376608 | T > A | p.K1502M |
| | | | | | | Missense | g.chr9:8492871 | T > G | p.T820P |
| | | | | | | Missense | g.chr9:8485273 | A > G | p.L1036P |
| | | | | | | Missense | g.chr9:8460547 | A > T | p.S1247T |
| | | | | | | Missense | g.chr9:8525016 | C > G | p.Q196H |
| | | | | | | Missense | g.chr9:8517884 | G > T | p.L503I |
| | | | | | | Missense | g.chr9:8485777 | G > T | p.L1014M |
| | | | | | | Missense | g.chr9:8460478 | C > G | p.V1270L |
| | | | | | | Missense | g.chr9:8471058 | C > G | p.L1147F |
| | | | | | | Missense | g.chr9:8518241 | T > G | p.S384R |
| | | | | | | Missense | g.chr9:8524994 | T > C | p.K204E |
| | | | | | | Missense | g.chr9:8507393 | C > G | p.E529Q |
| | | | | | | Missense | g.chr9:8636759 | G > T | p.D50E |
| PTPRE | NM_006504 | 3 | 0 | 0 | 0.00% | | | | |
| PTPRF | NM_002840 | 4 | 12 | 12 | 3.46% | Missense | g.chr1:44058140 | T > C | p.F561L |
| | | | | | | Missense | g.chr1:44085375 | A > T | p.T1653S |
| | | | | | | Missense | g.chr1:44086249 | G > T | p.R1788L |
| | | | | | | Missense | g.chr1:44069435 | G > A | p.G871D |
| | | | | | | Missense | g.chr1:44075146 | G > A | p.R1317Q |
| | | | | | | Splice_Site | g.chr1:44084958 | G > T | p.S1549_splice |

TABLE 2-continued

| Annotated Gene | Reference GenBan Seq. | No. of Synonymous Mutations | No. of Non-synonymous Mutations | No. of Tumors with Mutations | Mutation Frequency | Mutation Type | Genomic Change | Allele Change | Amino Acid Change |
|---|---|---|---|---|---|---|---|---|---|
| | | | | | | Missense | g.chr1:44085815 | G > A | p.E1721K |
| | | | | | | Missense | g.chr1:44085423 | C > T | p.R1669W |
| | | | | | | Missense | g.chr1:44054597 | G > T | p.R292L |
| | | | | | | Missense | g.chr1:44058210 | C > T | p.A584V |
| | | | | | | Missense | g.chr1:44069632 | G > T | p.D937Y |
| | | | | | | Missense | g.chr1:44069731 | G > C | p.D970H |
| PTPRG | NM_002841 | 0 | 4 | 3 | 0.86% | Missense | g.chr3:62261572 | T > C | p.Y1164H |
| | | | | | | Missense | g.chr3:62254758 | A > G | p.N975D |
| | | | | | | Missense | g.chr3:62188887 | T > C | p.I473T |
| | | | | | | Missense | g.chr3:62257095 | G > A | p.R1016K |
| PTPRH | NM_002842 | 1 | 3 | 3 | 0.86% | Missense | g.chr19:55693137 | G > T | p.H1111Q |
| | | | | | | Missense | g.chr19:55707974 | G > A | p.R725W |
| | | | | | | Missense | g.chr19:55711682 | C > T | p.G448R |
| PTPRJ | NM_002843 | 1 | 7 | 7 | 2.02% | Missense | g.chr11:48166263 | A > T | p.Y871F |
| | | | | | | Missense | g.chr11:48181492 | A > T | p.E1150V |
| | | | | | | Missense | g.chr11:48158579 | A > C | p.D633A |
| | | | | | | Missense | g.chr11:48145371 | C > G | p.L275V |
| | | | | | | Missense | g.chr11:48181590 | A > T | p.T1183S |
| | | | | | | Nonsense | g.chr11:48166647 | C > G | p.S961* |
| | | | | | | Missense | g.chr11:48168496 | A > G | p.I994V |
| PTPRK | NM_002844 | 2 | 6 | 6 | 1.73% | Missense | g.chr6:128304104 | C > G | p.D1137H† |
| | | | | | | Missense | g.chr6:128505717 | T > A | p.H341L |
| | | | | | | Missense | g.chr6:128291404 | C > T | p.D1430N |
| | | | | | | Missense | g.chr6:128404886 | G > C | p.P517A |
| | | | | | | Missense | g.chr6:128304088 | G > A | p.A1141V |
| | | | | | | Missense | g.chr6:128385930 | T > A | p.T723S |
| PTPRM | NM_002845 | 4 | 12 | 11 | 3.17% | Missense | g.chr18:8085808 | G > A | p.R564Q |
| | | | | | | Missense | g.chr18:8069752 | G > C | p.E401Q |
| | | | | | | Missense | g.chr18:8143677 | G > A | p.E734K |
| | | | | | | Missense | g.chr18:8380391 | C > T | p.S1282F |
| | | | | | | Missense | g.chr18:7888335 | C > A | p.A143E |
| | | | | | | Nonsense | g.chr18:8113617 | G > T | p.E664* |
| | | | | | | Missense | g.chr18:7955122 | C > A | p.P281Q |
| | | | | | | Missense | g.chr18:8379247 | G > T | p.C1219F |
| | | | | | | Missense | g.chr18:8296397 | A > C | p.D916A |
| | | | | | | Missense | g.chr18:8379226 | G > A | p.R1212Q |
| | | | | | | Missense | g.chr18:8370921 | G > C | p.E1017Q |
| | | | | | | Missense | chr18:8376134_83761 | GG > AA | p.G1075K |
| PTPRU | NM_005704 | 1 | 6 | 6 | 1.73% | Missense | g.chr1:29602185 | G > A | p.R457Q |
| | | | | | | Missense | g.chr1:29609426 | C > G | p.L703V |
| | | | | | | Missense | hr1:29644357_296443 | CG > TC | p.P1214L |
| | | | | | | Missense | g.chr1:29650167 | C > T | p.R1337W |
| | | | | | | Missense | g.chr1:29652139 | C > T | p.A1436V |
| | | | | | | Frame_Shift_Del | g.chr1:29611279 | delC | p.S739fs |
| PTPRZ1 | NM_002851 | 4 | 6 | 6 | 1.73% | Missense | g.chr7:121676716 | A > G | p.I1783V |
| | | | | | | Missense | g.chr7:121653325 | G > T | p.D1409Y |
| | | | | | | Missense | g.chr7:121636535 | T > C | p.I343T |
| | | | | | | Missense | g.chr7:121616905 | G > T | p.G207W |
| | | | | | | Nonsense | g.chr7:121691548 | A > T | p.K2051* |
| | | | | | | Frame_Shift_Ins | r7:121695040_121695 | insAT | p.N2143fs |

*Denotes mutation to a stop codon
†Denotes AA number change from previously reported cohort (Stransky et al, Science, 2011) for consistent numbering calling with the TCGA HNSCC cohort. Within each PTPR member, more than one mutation can be found in a single tumor. These are denoted in brown.

TABLE 3

Number of mutation of PTPR and PTPN family members across 17 examined cancers.

| Case # | Head & Neck 347 | Bladder 100 | Breast 507 | Cervix 36 | Colon 496 | Endometrioid 248 | Lung AD 230 | Lung SC 183 |
|---|---|---|---|---|---|---|---|---|
| Receptor type PTP | | | | | | | | |
| PTPRA | 2 | 1 | 1 | 0 | 6 | 9 | 2 | 0 |
| PTPRB | 12 | 3 | 5 | 0 | 17 | 31 | 16 | 18 |
| PTPRC | 15 | 4 | 1 | 0 | 37 | 17 | 14 | 8 |
| PTPRD | 13 | 5 | 12 | 0 | 29 | 36 | 38 | 18 |
| PTPRE | 0 | 1 | 2 | 0 | 9 | 12 | 1 | 3 |
| PTPRF | 12 | 3 | 5 | 2 | 20 | 26 | 6 | 8 |
| PTPRG | 4 | 3 | 3 | 1 | 21 | 21 | 8 | 4 |

TABLE 3-continued

Number of mutation of PTPR and PTPN family members across 17 examined cancers.

| | | | | | | | | |
|---|---|---|---|---|---|---|---|---|
| PTPRH | 3 | 3 | 3 | 0 | 11 | 15 | 8 | 15 |
| PTPRJ | 7 | 2 | 1 | 0 | 16 | 18 | 6 | 5 |
| PTPRK | 6 | 5 | 1 | 1 | 35 | 26 | 3 | 6 |
| PTPRM | 12 | 3 | 3 | 2 | 44 | 15 | 4 | 6 |
| PTPRN | 5 | 2 | 0 | 0 | 14 | 7 | 10 | 9 |
| PTPRN2 | 4 | 1 | 2 | 3 | 22 | 14 | 13 | 7 |
| PTPRO | 6 | 3 | 3 | 0 | 6 | 16 | 5 | 11 |
| PTPRQ | 0 | 0 | 2 | 0 | 31 | 33 | 0 | 2 |
| PTPRR | 4 | 1 | 2 | 0 | 20 | 17 | 7 | 8 |
| PTPRS | 6 | 1 | 2 | 0 | 29 | 22 | 7 | 3 |
| PTPRT | 20 | 6 | 2 | 1 | 45 | 19 | 21 | 18 |
| PTPRU | 6 | 2 | 5 | 0 | 35 | 17 | 5 | 10 |
| PTPRZ1 | 6 | 6 | 5 | 1 | 45 | 46 | 24 | 9 |
| # mutation | 143 | 55 | 60 | 11 | 492 | 417 | 198 | 168 |
| # case with mutation | 104 | 41 | 54 | 9 | 175 | 80 | 107 | 83 |
| % case with mutation | 30.0% | 41.0% | 10.7% | 25.0% | 35.3% | 32.3% | 46.5% | 45.4% |
| Non-receptor type PTP | | | | | | | | |
| PTPN1 | 2 | 0 | 0 | 0 | 11 | 5 | 2 | 2 |
| PTPN2 | 2 | 1 | 2 | 1 | 8 | 5 | 1 | 0 |
| PTPN3 | 5 | 5 | 0 | 1 | 15 | 18 | 2 | 3 |
| PTPN4 | 2 | 5 | 2 | 0 | 12 | 15 | 7 | 4 |
| PTPN5 | 0 | 0 | 3 | 0 | 9 | 8 | 8 | 1 |
| PTPN6 | 1 | 0 | 0 | 0 | 6 | 5 | 2 | 0 |
| PTPN7 | 2 | 1 | 2 | 0 | 3 | 6 | 0 | 1 |
| PTPN8 | 3 | 3 | 0 | 0 | 6 | 7 | 1 | 4 |
| PTPN11 | 0 | 0 | 1 | 0 | 12 | 8 | 3 | 4 |
| PTPN12 | 3 | 3 | 3 | 1 | 19 | 16 | 2 | 2 |
| PTPN13 | 9 | 4 | 4 | 5 | 37 | 30 | 4 | 9 |
| PTPN14 | 11 | 3 | 4 | 1 | 21 | 26 | 4 | 5 |
| PTPN18 | 0 | 0 | 1 | 0 | 4 | 5 | 1 | 5 |
| PTPN20A* | 0 | 0 | 0 | 0 | 0 | 0 | 0 | 0 |
| PTPN20B* | 0 | 0 | 0 | 0 | 1 | 0 | 0 | 0 |
| PTPN21 | 7 | 4 | 0 | 1 | 15 | 13 | 1 | 2 |
| PTPN22 | 4 | 6 | 8 | 0 | 6 | 15 | 1 | 3 |
| PTPN23 | 5 | 0 | 0 | 0 | 17 | 14 | 3 | 2 |
| # mutation | 56 | 35 | 30 | 10 | 202 | 196 | 42 | 47 |
| # case with mutation | 49 | 27 | 28 | 7 | 91 | 55 | 35 | 41 |
| % case with mutation | 14.1% | 27.0% | 5.5% | 19.4% | 18.3% | 22.2% | 15.2% | 22.4% |

| Case # | Ovary 456 | Prostate 83 | Stomach 151 | AML 199 | GBM 311 | Skin 219 | Thyroid 324 | Kidney 424 |
|---|---|---|---|---|---|---|---|---|
| Receptor type PTP | | | | | | | | |
| PTPRA | 0 | 0 | 7 | 0 | 2 | 5 | 0 | 2 |
| PTPRB | 2 | 1 | 15 | 0 | 2 | 64 | 1 | 4 |
| PTPRC | 3 | 0 | 18 | 0 | 2 | 24 | 1 | 6 |
| PTPRD | 6 | 2 | 25 | 0 | 3 | 56 | 2 | 2 |
| PTPRE | 0 | 0 | 2 | 1 | 1 | 11 | 0 | 0 |
| PTPRF | 5 | 0 | 15 | 0 | 3 | 22 | 0 | 3 |
| PTPRG | 6 | 0 | 13 | 1 | 1 | 9 | 0 | 2 |
| PTPRH | 3 | 1 | 2 | 1 | 5 | 14 | 0 | 2 |
| PTPRJ | 2 | 1 | 16 | 0 | 0 | 8 | 1 | 4 |
| PTPRK | 3 | 0 | 15 | 0 | 1 | 32 | 1 | 3 |
| PTPRM | 3 | 0 | 21 | 0 | 2 | 7 | 0 | 3 |
| PTPRN | 0 | 0 | 7 | 1 | 0 | 10 | 0 | 2 |
| PTPRN2 | 3 | 0 | 11 | 0 | 1 | 26 | 0 | 3 |
| PTPRO | 2 | 1 | 8 | 0 | 1 | 11 | 2 | 1 |
| PTPRQ | 0 | 0 | 0 | 0 | 0 | 0 | 0 | 9 |
| PTPRR | 3 | 0 | 5 | 0 | 3 | 14 | 0 | 3 |
| PTPRS | 4 | 0 | 24 | 1 | 2 | 12 | 2 | 3 |
| PTPRT | 9 | 1 | 32 | 3 | 7 | 88 | 1 | 3 |
| PTPRU | 1 | 0 | 17 | 1 | 1 | 11 | 0 | 4 |
| PTPRZ1 | 13 | 0 | 21 | 0 | 4 | 15 | 4 | 8 |
| # mutation | 68 | 7 | 274 | 9 | 41 | 0 | 15 | 67 |
| # case with mutation | 65 | 7 | 81 | 8 | 39 | 137 | 15 | 61 |
| % case with mutation | 14.3% | 8.4% | 53.6% | 4.6% | 12.5% | 62.6% | 4.6% | 14.4% |
| Non-receptor type PTP | | | | | | | | |
| PTPN1 | 0 | 0 | 0 | 0 | 0 | 3 | 0 | 1 |
| PTPN2 | 0 | 0 | 2 | 0 | 1 | 2 | 0 | 1 |
| PTPN3 | 5 | 0 | 6 | 0 | 3 | 9 | 0 | 1 |
| PTPN4 | 3 | 0 | 6 | 0 | 0 | 6 | 0 | 4 |
| PTPN5 | 3 | 0 | 1 | 1 | 0 | 9 | 0 | 2 |
| PTPN6 | 0 | 0 | 3 | 0 | 1 | 2 | 0 | 3 |
| PTPN7 | 0 | 0 | 2 | 0 | 0 | 2 | 0 | 1 |
| PTPN8 | 0 | 0 | 3 | 0 | 0 | 7 | 0 | 0 |

TABLE 3-continued

Number of mutation of PTPR and PTPN family members across 17 examined cancers.

| PTPN11 | 1 | 0 | 4 | 7 | 4 | 8 | 0 | 1 |
|---|---|---|---|---|---|---|---|---|
| PTPN12 | 3 | 0 | 4 | 0 | 1 | 3 | 0 | 4 |
| PTPN13 | 5 | 1 | 17 | 1 | 1 | 9 | 1 | 7 |
| PTPN14 | 0 | 1 | 1 | 2 | 0 | 16 | 0 | 2 |
| PTPN15 | 4 | 0 | 3 | 0 | 1 | 5 | 4 | 6 |
| PTPN20A* | 0 | 0 | 0 | 0 | 0 | 0 | 0 | 0 |
| PTPN20B* | 0 | 0 | 0 | 0 | 0 | 0 | 0 | 0 |
| PTPN21 | 4 | 2 | 8 | 0 | 0 | 5 | 2 | 2 |
| PTPN22 | 1 | 0 | 4 | 0 | 1 | 14 | 1 | 1 |
| PTPN23 | 0 | 0 | 12 | 1 | 0 | 4 | 0 | 1 |
| # mutation | 29 | 4 | 76 | 12 | 13 | 104 | 8 | 37 |
| # case with mutation | 27 | 4 | 37 | 12 | 12 | 70 | 8 | 33 |
| % case with mutation | 5.9% | 4.8% | 24.5% | 6.0% | 3.9% | 32.0% | 2.5% | 7.8% |

*PTPN20A and PTPN20B case for same protein

TABLE 4

Sequence and structure characteristics of HNSCC-associated PTPRT mutations.

| Amino Acid Change | Prior Occurrence[a] | Change in Charge[b] | Change in Size[c] |
|---|---|---|---|
| p.A1022E | n | −1 | 4 |
| p.R1040L | n | −1 | −3 |

[a]Indicates whether the mutation has been observed in known sequences (inferred from the analysis of the multiple sequence alignment, MSA, of 34 sequences using Consurf package[13].
[b]Electric charge difference between the mutated and the wild type forms, in units of the electron charge; large changes (of 2; boldface) could affect structure and function.
[c]Change in the number of atoms upon mutation.

7.4 References

1. Groesser, L., et al. Nat Genet 44, 783-7 (2012).
2. Paez, J. G., et al. Science 304, 1497-500 (2004).
3. Veeriah, S., et al. Proc Natl Acad Sci USA 106, 9435-40 (2009).
4. Zhang, X., et al. Proc Natl Acad Sci USA 104, 4060-4 (2007).
5. Barr, A. J., et al. Cell 136, 352-63 (2009).
6. Sali, A. and Blundell, T. L. J Mol Biol 234, 779-815 (1993).
7. Wang, Z., et al. Science 304, 1164-6 (2004).
8. Lim, S. H., et al. EMBO J 28, 3564-78 (2009).
9. Cerami, E., et al. Cancer discovery 2, 401-4 (2012).
10. Stransky, N., et al. Science 333, 1157-60 (2011).
11. Cerami, E., et al. Cancer Discov 2, 401-4 (2012).
12. Lui, V. W., et al. Mol Pharmacol 71, 1435-43 (2007).
13. Ashkenazy, H., et al. Nucl. Acids Res 38, 529-533 (2010)

8. EXAMPLE 3: PTPR MUTATION ENHANCES SENSITIVITY TO STAT3 PATHWAY INHIBITORS

To determine if PTPR mutation enhances sensitivity to STAT3 pathway inhibitors, HNSCC cell lines harboring endogenous PTPR mutation were compared with cell lines containing WT PTPRs. Cells were plated at equal density ($3\times10^4$/well), treated with various concentration of the STAT3 inhibitors, Stattic (Sigma-Aldrich, MO), a small molecule inhibitor of STAT3 activation and dimerization, or JSI-124 (Calbiochem, MA) for 24 hours, followed by MTT assay (n=3). EC50 values were determined, with extrapolation at 20 μM, by GraphPad Prism 5 software. As shown in FIG. 1I, cells with endogenous mutant PTPRD (PE/CAPJ49, I1821V) were more sensitive to the growth inhibitory effects of Stattic compared with HNSCC cell lines with WT PTPRD [PE/CAPJ34(Clone 12)]. These results show that mutations of the PTPR family, specifically PTPRT and PTPRD, lead to increased STAT3 activation in HNSCC.

9. EXAMPLE 4: AZD1480 ABROGATES STAT3 ACTIVATION AND HNSCC GROWTH AND STAT3 SIGNALING IN VITRO AND IN VIVO

9.1 Results

In vivo studies have generally relied on xenograft tumors derived from implantation of immortalized HNSCC cell lines into immunocompromised mice. To generate a more clinically relevant platform to assess the antitumor effects of candidate therapies, human tumors were directly inoculated into NOD/SCID mice. To date, implanted tumors from 35 HNSCC patients were obtained according to previously described methods [1]. Twenty-six of these tumors have grown successfully in mice at a median time of 16 weeks (range 6-26 weeks) for a take rate of 74%. These tumors represent the diversity of HNSCC, including tumors arising in different anatomic sites (oral cavity, pharynx, larynx). Furthermore, these tumors have been passaged and expanded into larger numbers of mice to allow for therapeutic studies (20-40 tumors generated from 1 primary tumor implant). As shown in FIG. 12, treatment of heterotopic tumorgrafts derived from 2 HNSCC patient tumors (1 and 2; each expanded into 10 mice per group) with AZD1480, an ATP-competitive, oral, small molecule inhibitor of the JAK1 and JAK2 kinases, demonstrated antitumor effects. Although, JAK kinases are not reported to be mutated in HNSCC, activation of JAK1 or JAK2 in HNSCC cells leads to STAT3 tyrosine phosphorylation [2]. Inhibition of WT JAK2 is particularly potent, with an enzyme IC50<0.003 micromolar [3]. Similar antitumor effects were observed in tumorgrafts derived from two additional HNSCC tumors using the preclinical JAK/STAT inhibitor JSI-124.

The effect of AZD1480 on STAT3 tyrosine phosphorylation and cell growth was further assessed in a panel of HNSCC cell lines. As shown in FIG. 13, AZD1480 reduced pSTAT3 expression in a dose- and time-dependent manner and inhibited the proliferation of HNSCC cells with low micromolar EC50 concentrations (range 0.99-3.8 uM in 9 HNSC cell lines tested; data not shown). In addition, heterotopic xenografts derived from 2 representative HNSCC human tumors were growth inhibited in vivo by AZD1480 treatment in conjunction with decreased expression of pSTAT3 and STAT3 target genes. In addition, HNSCC cells harboring a PTPRD mutation (P311T) demonstrated decreased survival and STAT3 promoter activity when treated with AZD1480 compared with controls (FIG. 14).

9.2 References

1. Kim M P, Evans D B, Wang H, Abbruzzese J L, Fleming J B, Gallick G E. Generation of orthotopic and heterotopic human pancreatic cancer xenografts in immunodeficient mice. Nat Protoc. 2009; 4(11):1670-80.
2. Lee T L, Yeh J, Van Waes C, Chen Z. Epigenetic modification of SOCS-1 differentially regulates STAT3 activation in response to interleukin-6 receptor and epidermal growth factor receptor signaling through JAK and/or MEK in head and neck squamous cell carcinomas. Mol Cancer Ther. 2006; 5(1):8-19.
3. Ioannidis S, Lamb M L, Wang T, Almeida L, Block M H, Davies A M, et al. Discovery of 5-chloro-N2-[(1S)-1-(5-fluoropyrimidin-2-yl)ethyl]-N4-(5-methyl-1H-pyrazol-3-yl)pyrimidine-2,4-diamine (AZD1480) as a novel inhibitor of the Jak/Stat pathway. J Med Chem. 2011; 54(1): 262-76.

10. EXAMPLE 5: HRAS HOTSPOT MUTATION RESULTS IN HEIGHTENED SENSITIVITY TOWARDS PI3K TARGETING

10.1 Results

Increased PI3K signaling can also result from mutations in genes in the PI3K pathway such as p85, AKT, and HRAS, which has been reported to activate PI3K signaling [1]. To test whether increased PI3K signaling can be achieved by mutations in HRAS, a hotspot HRAS mutation found in our HNSCC cohort, HRAS(Q61K), was generated. Experiments were performed to determine the effect this mutation had on PI3K activation and response to PI3K pathway inhibition. As shown in FIG. 15, expression of this mutant form of HRAS led to a marked increased in pAKT expression and growth inhibition following treatment with the PI3K/mTOR inhibitor BEZ 235. These results provide support for the hypothesis that mutations in genes that activate the PI3K pathway in HNSCC enhance sensitivity to treatment with a PI3K pathway inhibitor(s).

10.2 References

1. Groesser L, Herschberger E, Ruetten A, Ruivenkamp C, Lopriore E, Zutt M, et al. Postzygotic HRAS and KRAS mutations cause nevus sebaceous and Schimmelpenning syndrome. Nat Genet. 2012; 44(7):783-7. Epub 2012/06/12. doi: 10.1038/ng.2316. PubMed PMID: 22683711.

Various publications are cited herein, the contents of which are hereby incorporated by reference in their entireties.

We claim:

1. A method of identifying a driver gene or mutation in a human head and neck squamous cell cancer comprising (i) providing a first cell and a second cell of human head and neck squamous cell carcinoma cell line UM-SCC47 that, when grown in culture medium having a serum concentration of 2 percent, has a slower growth rate than when grown in culture medium having a serum concentration of 10 percent, (ii) inserting a putative driver gene/mutation into the first cell, wherein the putative driver gene/mutation does not preexist in the first cell or in the second cell, (iii) culturing the first cell and the second cell in culture medium having a serum concentration between 0 and 5 percent, and (iv) comparing the growth rate of the first cell to the second cell, where the first cell being able to grow at an improved rate relative to the second cell indicates that the putative driver gene/mutation is a driver gene/mutation.

2. A method of identifying a driver gene or mutation in a human head and neck squamous cell cancer comprising (i) providing a first cell and a second cell of human head and neck squamous cell carcinoma cell line PCI-52 that, when grown in culture medium having a serum concentration of 2 percent, has a slower growth rate than when grown in culture medium having a serum concentration of 10 percent, (ii) inserting a putative driver gene/mutation into the first cell, wherein the putative driver gene/mutation does not preexist in the first cell or in the second cell, (iii) culturing the first cell and the second cell in culture medium having a serum concentration between 0 and 5 percent, and (iv) comparing the growth rate of the first cell to the second cell, where the first cell being able to grow at an improved rate relative to the second cell indicates that the putative driver gene/mutation is a driver gene/mutation.

3. The method of claim 1 or 2 where the putative driver gene/mutation is a wild-type or mutant form of a gene that functions in a signaling pathway selected from the group consisting of the JAK/STAT signaling pathway, the MAPK pathway, the PI3K signaling pathway, and a combination thereof.

4. A method of identifying a driver gene or mutation that increases sensitivity to a therapeutic agent comprising (i) applying the therapeutic agent to a plurality of cells, each of which (a) is a cell of a head and neck squamous cell carcinoma cell line selected from the group consisting of UM-SCC47 and PCI-52 that, prior to having a driver gene/mutation inserted, when grown in culture medium having a serum concentration of 2 percent has a slower growth rate than when grown in culture medium having a serum concentration of 10 percent and (b) into which the driver gene or mutation has been inserted; wherein certain cells express different driver genes/mutations, (ii) culturing the plurality of cells in culture medium having a serum concentration between 0 and 5 percent, and then (iii) comparing the growth rate of cells having different driver genes/mutations, where if one cell that expresses a first driver gene or mutation is able to grow at a reduced rate and/or exhibit reduced survival in the presence of the therapeutic agent relative to a cell that expresses a different, second, driver gene/mutation in the presence of the same therapeutic agent, then the first driver gene/mutation is indicated to be associated with increased sensitivity to the therapeutic agent.

5. The method of claim 4 where the one or more cells are head and neck squamous cell carcinoma cells the growth of which is serum dependent.

6. The method of claim 4 where different driver genes/mutations are contained in different cell lines.

7. The method of claim 5 where different driver genes/mutations are contained in different cell lines.

* * * * *